(12) United States Patent
Van Lue

(10) Patent No.: US 7,780,639 B2
(45) Date of Patent: Aug. 24, 2010

(54) MAGNETIC DEVICES AND APPARATUS FOR MEDICAL/SURGICAL PROCEDURES AND METHODS FOR USING SAME

(76) Inventor: Stephen J. Van Lue, 1150 Doyle Cir., Santa Clara, CA (US) 95054

( * ) Notice: Subject to any disclaimer, the term of this patent is extended or adjusted under 35 U.S.C. 154(b) by 1111 days.

(21) Appl. No.: 10/578,804

(22) PCT Filed: Nov. 9, 2004

(86) PCT No.: PCT/US2004/037502

§ 371 (c)(1),
(2), (4) Date: May 9, 2006

(87) PCT Pub. No.: WO2005/048814

PCT Pub. Date: Jun. 2, 2005

(65) Prior Publication Data

US 2007/0142780 A1    Jun. 21, 2007

Related U.S. Application Data

(60) Provisional application No. 60/519,116, filed on Nov. 12, 2003, provisional application No. 60/520,406, filed on Nov. 14, 2003.

(51) Int. Cl.
*A61M 5/00* (2006.01)
(52) U.S. Cl. .................................................. 604/264
(58) Field of Classification Search .......... 606/167, 606/185, 213; 604/184, 264
See application file for complete search history.

(56) References Cited

U.S. PATENT DOCUMENTS 3,893,651 A * 7/1975 Uecker ..................... 251/82

(Continued)

FOREIGN PATENT DOCUMENTS

| DE | 2800607 | 1/1978 |
|---|---|---|
| FR | 2 719 210 | 11/1995 |
| JP | 2000/000246 | 1/2000 |
| WO | WO01/43812 | 6/2001 |

OTHER PUBLICATIONS

"Einweg-Sicherhetis-Trokar," Product brochure, MGB Endoskopische Gerate GmbH, Oct. 12, 2003.

(Continued)

*Primary Examiner*—Kevin T Truong
(74) *Attorney, Agent, or Firm*—David M. Quinlan, P.C

(57) ABSTRACT

One embodiment of the invention comprises a trocar and a reducer cap that magnetically attaches to the trocar. The trocar and the cap each include a magnetic member, at least one of which is a first magnet, and the other of which is either a second magnet or a non-magnetized magnetically permeable member. Including a magnet of sufficient strength in the trocar and/or the cap will create a magnetic field that automatically holds a surgical instrument having a magnetically permeable member at its tip in axial alignment with the cap or trocar lumen. Introduction of the surgical instrument into the lumen can be further facilitated by providing the trocar or cap lumen with a funnel-shaped opening. A lumen seal can be provided by one or more compliant toroidal seal members that expand radially inwardly when compressed axially by the magnetic attraction between the cap and trocar. The alignment feature is particularly advantageous when incorporated in a mini-trocar having a lumen on the order of 1-3 mm in diameter. In that case, a trocar cap can be a small disc magnetically attracted to the trocar to cover the lumen. Magnetic aligning devices according to the invention can be used internally of a patient or transdermally. Another embodiment of the invention is an ostium plug with a lumen therethrough that can be used in tubal sterilization. The plug is permanently implanted in the patient, but a cap is coupled magnetically to the proximal end of the plug to permit reopening of the lumen when desired.

22 Claims, 15 Drawing Sheets

U.S. PATENT DOCUMENTS

| | | | |
|---|---|---|---|
| 3,961,632 A | 6/1976 | Moossun | |
| 4,338,937 A * | 7/1982 | Lerman | 604/255 |
| 4,535,773 A | 8/1985 | Yoon | |
| 4,809,713 A | 3/1989 | Grayzel | |
| 5,338,307 A | 8/1994 | Stephens et al. | |
| 5,397,314 A | 3/1995 | Farley et al. | |
| 5,417,701 A | 5/1995 | Holmes | |
| 5,423,761 A | 6/1995 | Hein et al. | |
| 5,591,186 A | 1/1997 | Wurster et al. | |
| 5,758,667 A | 6/1998 | Slettenmark | |
| 5,797,888 A | 8/1998 | Yoon | |
| 5,824,009 A | 10/1998 | Fukuda et al. | |
| 5,882,344 A | 3/1999 | Stouder, Jr. | |
| 5,916,198 A | 6/1999 | Dillow | |
| 6,035,870 A * | 3/2000 | Monch | 134/59 |
| 6,068,637 A | 5/2000 | Popov et al. | |
| 6,159,224 A | 12/2000 | Yoon | |
| 6,248,060 B1 | 6/2001 | Buess et al. | |
| 6,352,543 B1 | 3/2002 | Cole | |
| 6,357,443 B1 | 3/2002 | Loy | |
| 6,450,950 B2 | 9/2002 | Irion | |
| 6,522,909 B1 | 2/2003 | Garibaldi et al. | |
| 6,524,303 B1 | 2/2003 | Garibaldi et al. | |
| 6,537,290 B2 * | 3/2003 | Adams et al. | 606/167 |
| 6,652,540 B1 | 11/2003 | Cole et al. | |
| 6,655,386 B1 | 12/2003 | Makower et al. | |
| 6,712,810 B2 | 3/2004 | Harrington et al. | |
| 7,546,855 B2 * | 6/2009 | Rodewald | 141/348 |

OTHER PUBLICATIONS

"Adipositas-Instrumenten-Set," Product borchure, Richard Wolf.

Written Opinion with International Search Report, PCT/US04,37502, Sep. 27, 2006.

Supplementary Partial European Search Report, EP Appln. EP 04 81 9079. May 28, 2010.

* cited by examiner

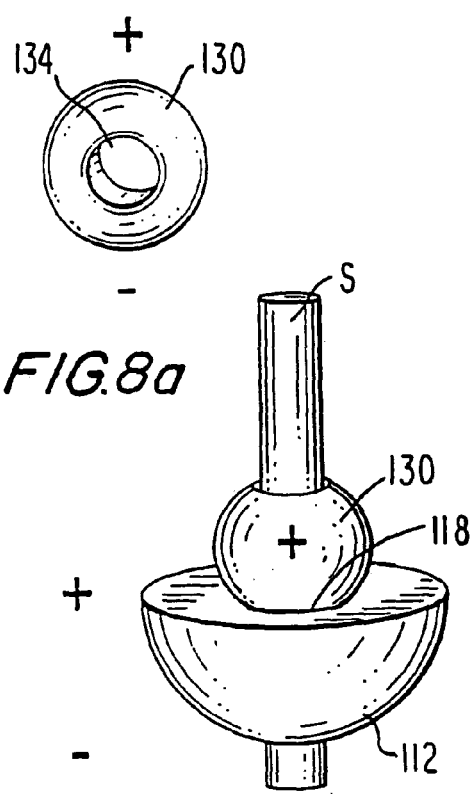
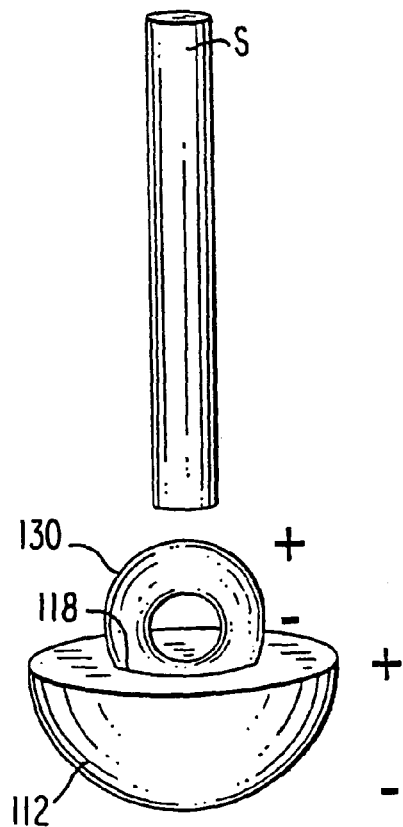
FIG.8a
FIG.8b
FIG.8c

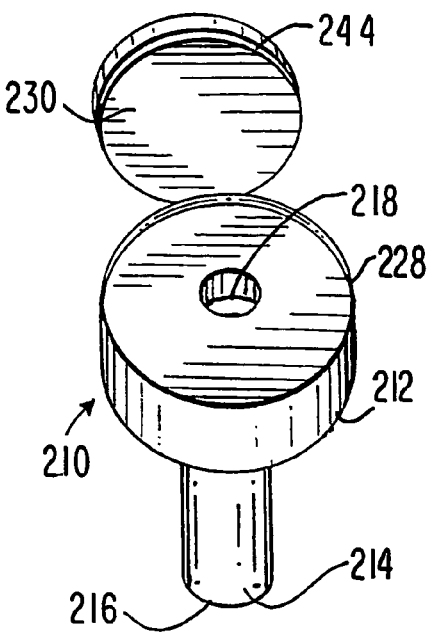
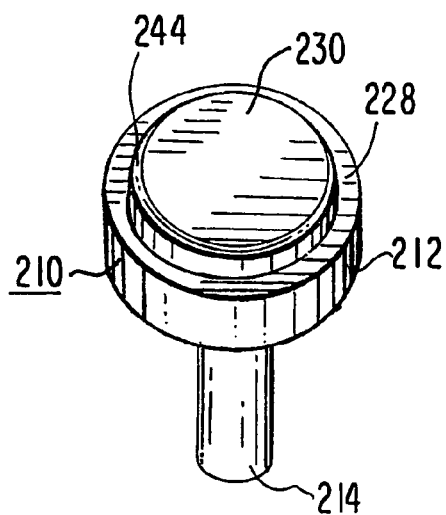
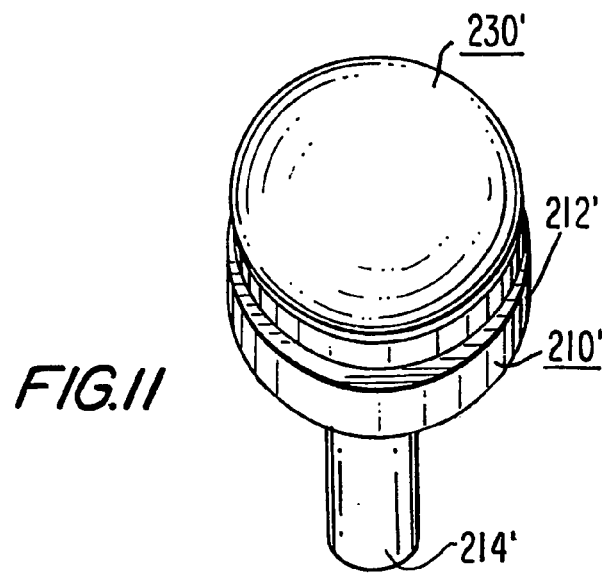
FIG.9
FIG.10
FIG.11

MAGNETIC DEVICES AND APPARATUS FOR MEDICAL/SURGICAL PROCEDURES AND METHODS FOR USING SAME

CROSS-REFERENCE TO RELATED APPLICATIONS

This application claims the benefit of U.S. provisional application No. 60/519,116, filed Nov. 12, 2003, and U.S. provisional application No. 60/520,406, filed Nov. 14, 2003, both of which applications are incorporated herein by reference.

BACKGROUND OF THE INVENTION

1. Field of the Invention

The present invention relates to medical/surgical devices and apparatus and methods of using them, and more particularly, to such apparatus and devices incorporating magnets.

2. Description of Related Art

Trocars are commonly used to provide access to internal body parts during surgery. In its most basic form, a conventional surgical trocar includes a base having a depending elongated cannula, with a lumen extending axially of the cannula and through the base. In use, the cannula extends into a body cavity of the patient to enable a surgical procedure to be performed without a large incision or major invasion of the interior of the patient's body. The trocar base remains outside the patient. The surgeon passes through the trocar lumen a surgical instrument, such as endoscope or any other device typically used in this type of minimally invasive surgery, to position it within the patient's body at the desired location. Examples of this type of trocar assembly are shown in U.S. Pat. No. 4,535,773, U.S. Pat. No. 5,338,307, U.S. Pat. No. 5,397,314, U.S. Pat. No. 5,882,344, U.S. Pat. No. 5,423,761, German Patent Publ. No. 28 00 607, French Patent No. 2,719,210, Japanese Patent Abstract No. 2000/000246, and International Appln. No. WO01/43812.

This type of minimally invasive surgical procedure may require that the anatomical region or body cavity implicated in the procedure be insufflated with a gas, such as carbon dioxide, or in some cases a liquid, such as a saline solution. Insufflation distends the region or cavity in order to provide the surgeon with sufficient space to carry out procedures such as laparoscopy, arthroscopy, hysteroscopy and hydrolaparascopy. Conventionally, the patient is insufflated through the trocar or through a Veress needle before the procedure is begun. It is preferable that adequate insufflation be maintained, to ensure that the surgeon's vision of the target area remains unimpaired throughout the procedure and to prevent the necessity of interrupting the procedure to reinsufflate the patient. For that reason, a trocar will typically include some sort of valve to prevent the escape of the insufflating gas. However, the construction of known valves normally prevents them from sealing perfectly around a surgical instrument shaft, which can result in the escape of insulating gas from the patient. Examples of trocar lumen valves and seals are shown in the above-mentioned U.S. Pat. No. 4,535,773, U.S. Pat. No. 5,397,314, U.S. Pat. No. 5,423,761, German Patent Publ. No. 28 00 607, French Patent No. 2,719,210, Japanese Patent Abstract No. 2000/000246, and International Appln. No. WO01/43812, and also in U.S. Pat. No. 5,916,198.

In constructions where the trocar valve or seal may permit insufflation gas to escape around the instrument shaft, insufflation pressure can be maintained when the surgical instrument is in place by using a reducer cap at the proximal end of the trocar base. U.S. Pat. No. 5,338,307 describes a reducer cap that is capable of movement into position to present to the surgical instrument an opening that fits closely to the instrument shaft. While the cap in this patent serves its intended purpose, it is cumbersome to manipulate into and out of position. The kinds of minimally invasive procedures with which these trocars are used are typically performed in darkened operating rooms, so that the surgeon can see more clearly a video feed from the surgical site within the patient's body. However, in a darkened room it is more difficult to perform the manual manipulation required to put the reducer cap described in U.S. Pat. No. 5,338,307 onto the trocar in the first place, and to remove it from the trocar if that becomes necessary and then replace it again if need be.

Conventional reducer caps may require the surgeon or an assistant to use two hands to place the cap and correctly orient it for attachment to the trocar. This complicates the situation when the surgeon needs to introduce a curved needle and suture, or remove tissue, through the trocar, because these maneuvers may require that the trocar cap be removed and then subsequently replaced. If replacement of the cap requires the surgeon and/or the assistant to release their hold on the surgical instruments and look away from the video monitor displaying the operative site within the patient to manipulate the trocar cap, it interrupts the procedure. If the procedure is being performed in a low-light environment, using these known reducer caps is even more disruptive because it will be difficult to see the cap and trocar clearly after looking at a relatively bright video monitor. To compensate for this, low intensity illumination can be projected at the trocar, but that in turn can detract from the clarity and sharpness perceived on the video monitor. It would therefore be advantageous to have a cap that can be easily and quickly removed and replaced on the trocar without requiring precise manipulation by the surgical team so that cap removal/replacement does not disrupt ongoing surgical procedures.

At the same time, there is a need to provide the trocar with sufficient lateral stability when in place in a patient. If the trocar base extends too far outside the patient, the resulting high profile can make it difficult to maintain the seal between the patient's skin and the trocar cannula. Incorporating prior art lumen seals into the trocar base tends to increase the length of the base, thus resulting in a higher profile trocar when in use. Another important consequence of this instability is that it can make it very difficult for the surgeon to introduce the instrument through the lumen of the trocar cap. As discussed above, a purpose of the cap is to present to the surgical instrument a lumen that fits snugly around the instrument shaft. If the trocar is prone to movement, it makes it even more difficult to align the instrument shaft with the tightly fitting cap lumen.

Another stability problem presents itself when a trocar of a given length cannot be inserted into the patient far enough so that the underside of the trocar base rests snugly against the patient's skin. U.S. Pat. No. 5,882,344 explains that this can happen if the trocar cannula is sufficiently long to penetrate the patient's internal organs. Partial insertion of the trocar will solve the problem, but at the expense of preventing the trocar base from bearing on the patient's skin, thus sacrificing trocar stability. U.S. Pat. No. 5,882,344 provides an adjustable length cannula to address this problem, but the decreased stability from incorporating a lumen valve into the trocar remains.

Another aspect of minimally invasive surgical procedures is that it is sometimes necessary to align surgical instruments across an internal tissue boundary. For example, it is often necessary to pass a suturing needle through an internal tissue boundary at a precise location. There are numerous devices and techniques employing magnetism to align, manipulate, or effect placement of surgical and medical devices. Examples are shown in U.S. Pat. Nos. 3,961,632, 4,809,713, 5,417,701, 5,824,009, 6,068,637, 6,159,224, 6,450,950, 6,522,909, 6,524,303, 6,352,543, 6,652,540, and 6,655,386. However, none of those devices or the manner of using them appears to be readily adaptable to providing alignment of a surgical device such as a suturing needle blindly across an internal tissue boundary.

A related problem is encountered with a vascular access port ("VAP") implanted in a patient to enable repeated administration of medications without requiring a vein, artery, or other anatomical structure to be punctured each time. The implanted VAP is connected permanently to a vascular structure or other anatomical region and the medication is introduced into the VAP with a hypodermic needle. Typical VAPs have a membrane or septum, and a hypodermic needle is used to puncture the patient's skin and introduce the medication through the septum into a plenum in the VAP. For proper administration of the medication, the hypodermic needle must be lined up with the septum before the needle is passed through the patient. U.S. Pat. No. 5,758,667 discloses a magnetic device for locating the septum of an implanted medication dispenser. While this device should be able to locate the septum under optimum conditions, it is constructed in a way that makes it somewhat cumbersome to introduce the medication once the implanted septum is located. It is also susceptible to misalignment of the hypodermic needle and the septum if the relative position of the VAP device shifts under the patient's skin.

Another medical procedure that is often performed is the implantation of a plug into an internal ostium of a subject, such as a tubal sterilization procedure using ostium plugs in the openings of the subject's Fallopian tubes. These plugs typically include barbs that engage the internal walls of the tubal ostia, causing minor trauma. This trauma, along with local tissue reaction to biomaterials within the construction of the plug, create scar tissue that firmly holds the plug in place. U.S. Pat. Nos. 6,357,443 and 6,712,810 discuss examples of such plugs. Such tubal sterilization procedures are not easily reversible. For example, to reverse a sterilization effected by the technique discussed in U.S. Pat. No. 6,357,443, the entire plug must be removed. Tubal sterilizations of this type would be more attractive to patients if there were a more reliable and simpler technique for reversing the sterilization.

SUMMARY OF THE INVENTION

It is an object of the invention to provide apparatuses, devices and methods employing magnetism in ways that avoid problems encountered with the prior art, as discussed above, and that facilitate manipulation and alignment of various surgical apparatuses and devices.

In accordance with one aspect of the invention, a trocar assembly comprises a trocar having a distal end, a proximal end, and a trocar lumen from the proximal end to the distal end, and a trocar cap for removable attachment to the proximal end of the trocar body, the cap having a cap lumen, wherein the trocar and the trocar cap each include a magnetic member, at least one of the magnetic members comprising a first magnet, and the other magnetic member comprising a second magnet or a non-magnetized magnetically permeable member (meaning a member of a material that is attracted to a magnet), the magnetic members being positioned on the cap and the trocar for magnetically securing the cap to the proximal end of the trocar with the cap lumen in alignment with the trocar lumen.

The invention also contemplates such a trocar assembly further comprising at least one of a cap valve member including a compliant toroidal body disposed in the cap and a trocar valve member including a compliant toroidal body disposed in the trocar base, wherein the toroidal body has a central opening and is disposed for compression axially when the cap is magnetically secured to the base thereby closing the central opening when a surgical instrument is not present in the lumen.

In another aspect of the invention, a trocar comprises an elongated cannula for extending through a tissue boundary, the cannula having a distal end for placement on one side of the tissue boundary and a proximal end for placement on another side of the tissue boundary and a trocar base disposed at said proximal end of the cannula, with a trocar lumen extending axially of the base from a proximal end thereof to the distal end of the cannula, and a magnet in the base for creating a magnetic field generally axially aligned with the lumen and having a predetermined strength for holding a distal end of an elongated surgical instrument in place on axial alignment with the lumen.

This aspect of the invention further contemplates a trocar assembly with a cap as discussed above, wherein the cap includes a magnet for creating a magnetic field generally axially aligned with the cap lumen and having a predetermined strength for holding a distal end of an elongated surgical instrument in place on axial alignment with the cap lumen. The magnet may comprise an annular disc surrounding the cap or trocar lumen, and the lumen can provide a funnel-shaped opening for entry of the distal end of the surgical instrument.

In yet another aspect of the invention, a valve for sealing a lumen that can accept a surgical instrument includes a valve body comprising a magnet having a depression defining a body with an axis of rotation and a lumen with an axis generally perpendicular to the axis of rotation of the depression, the valve body having a magnetic field with a polar axis disposed at a predetermined angle relative to the valve body lumen axis, and a valve member seated in the depression and comprising a magnet defining a solid body with an axis of rotation parallel to axis of rotation of the depression and a lumen with an axis generally perpendicular to the axis of rotation of the valve member, the valve member having a magnetic field with a polar axis disposed at a predetermined angle relative to the valve member lumen axis, wherein the angles of the polar axes of the valve member and the valve body relative to the respective lumens thereof are chosen such that the valve body will automatically rotate in the depression to assume one of (i) a position in which the lumens are aligned and (ii) a position in which the valve member blocks the valve body lumen.

In a yet ether aspect of the invention, a mini-trocar assembly comprises a trocar including an elongated, generally circular cannula having a diameter of about 2-5 mm for extending through a tissue boundary, the cannula having a distal end for placement on one side of the tissue boundary and a proximal end for placement on another side of the tissue boundary, a base having a generally annular shape about 10-20 mm in diameter and 8-15 mm wide in an axial direction and being disposed at the proximal end of the cannula, the base including a permanent magnet at a proximal end thereof, and a trocar lumen extending from the proximal end of the base to the distal end of the cannula, and a cap including a magnetic member comprising one of a magnet and a non-magnetized magnetically permeable member, the cap fitting within a mating receptacle in a proximal end of the base.

In a still further aspect of the invention, a method of aligning a surgical instrument with a trocar lumen includes the steps of providing a trocar including an elongated cannula extending through a tissue boundary of a patient, the cannula having a distal end for placement on one side of the tissue boundary and a proximal end for placement on another side of the tissue boundary, a base disposed at the proximal end of the cannula, the base including a magnet at the proximal end thereof, and a trocar lumen extending from the proximal end of the base to the distal end of the cannula, attaching to a distal end of a surgical instrument a disc-shaped aligning device comprising a permanent magnet by positioning in a lumen of the aligning device the magnetically permeable member of the instrument, magnetically coupling a disc-shaped capping device comprising a magnetic member to the aligning device at a proximal side thereof to hold the surgical instrument between the aligning device and the capping device, and bringing the distal end of the surgical instrument into proximity with the base so that the aligning device moves into contact with the proximal end of the base and the distal end of the surgical instrument is introduced into the trocar lumen, while maintaining the capping device in contact with the surgical instrument and the aligning device.

This aspect of the invention contemplates the further step of withdrawing the surgical instrument from the trocar and allowing the capping device to remain magnetically coupled to the aligning device in a position capping the trocar lumen.

In yet a further aspect of the invention, a method of aligning a surgical instrument across an internal tissue boundary of a patient includes the steps of:

(1) providing a generally cylindrical magnetic aligning device with an axial opening at one end thereof, the aligning device comprising a magnet with a polar axis aligned with the axis of the aid opening, (2) illuminating one side of the tissue boundary with an illuminating device for providing a visual indication of the location of the opening through the tissue boundary, (3) grasping with an end effector at a distal end of a surgical instrument a flexible portion of a surgical device including a magnetic member having an elongated axis, (4) positioning the surgical device proximate to the visual indication of the opening location for aligning the axis of the surgical device with the polar axis of the aligning device, and (5) forcing the surgical device through the tissue boundary in a direction generally parallel to the axis of the surgical device.

This aspect of the invention further contemplates a method in which the surgical device is a suturing needle pointed at two ends, the flexible portion is a suture attached to the needle, the step (3) comprises grasping the suture near a point of attachment to the needle with the end effector, the step (4) comprises positioning the needle by manipulating the surgical instrument at a proximal end thereof external of the patient, and the magnetic aligning device includes a gripping device for gripping an end of the needle protruding through the tissue boundary, wherein the method further includes the steps of:

(6) gripping an end of the needle with the gripping device and pulling the needle through to the other side of the tissue boundary, (7) moving the aligning device to a second location determined using the illuminating device, (8) forcing the needle through the tissue boundary at second location and grasping the needle using the end effector and pulling the needle through the tissue boundary to the first-mentioned side thereof, and (9) repeating steps (2) to (8) a predetermined number of times.

In a still further aspect of the invention, an apparatus for aligning an external needle with an implantable medication dispenser comprises a dispenser including a connector for connecting a plenum of the dispenser to an internal vascular body of a patient, a septum through which medication is introduced into the plenum using the needle, an attachment member for securing the dispenser to an internal structure of a patient with the septum accessible through the patient's skin, and a first magnetic member disposed in a predetermined relation to the septum, and a coupling device including a second magnetic member for magnetically coupling with the first magnetic member and a locating hole disposed in a predetermined relation to the second magnetic member, the septum and the hole being aligned when the first and second magnetic members are magnetically coupled, wherein at least one of the magnetic members comprises a first magnet, and the other of the magnetic members comprises a second magnet or a non-magnetized magnetically permeable member.

In a yet further aspect of the invention, an implantable plug comprises a plug member including barb members for gripping the walls of a tube when the plug is inserted into a tubal ostium of a patient, the plug comprising a central lumen from a distal end to a proximal end thereof, and a first magnetic member at the proximate end of the lumen for cooperating with a second magnetic member on a cap for blocking the lumen, wherein at least one of the magnetic members comprises a first magnet, and the other of the magnetic members comprising a second magnet or a non-magnetized magnetically permeable member.

BRIEF DESCRIPTION OF THE DRAWINGS

The objects of the invention will be better understood from the detailed description of its preferred embodiments which follows below, when taken in conjunction with the accompanying drawings, in which like numerals refer to like features throughout. The following is a brief identification of the drawing figures used in the accompanying detailed description.

FIGS. 8a to 8c are perspective schematic representations of a third embodiment of the present invention comprising a lumen valve arrangement, wherein FIG. 8a shows a magnetic valve member comprising a part of the lumen valve of this embodiment, FIG. 8b shows the valve member in place in a magnetic valve body that forms a part of the lumen valve, in which the valve is in an open position with a surgical instrument extending therethrough, and FIG. 8c shows the lumen valve of this embodiment is its closed position, which the valve occupies when the surgical instrument is removed.

FIGS. 9 and 10 are perspective schematic depictions of a fourth embodiment of the invention comprising a mini-trocar assembly, wherein FIG. 9 shows a trocar cap in an open position removed from the trocar to permit access to the trocar lumen, and FIG. 10 shows the cap in a closed position in which it is magnetically secured to the trocar to seal the trocar lumen.

FIG. 11 is a perspective view of an alternate version of the mini-trocar assembly in FIGS. 9 and 10, wherein the trocar cap is spherical.

FIGS. 12 to 14 are perspective schematic representations of a fifth embodiment of the invention, in which FIG. 12 shows magnetic securing and sealing elements in place at the end of a surgical instrument, FIG. 13 shows the surgical instrument after introduction into the lumen of a trocar, and FIG. 14 illustrates how the securing and sealing members cooperate to seal the trocar lumen when the surgical instrument is withdrawn.

FIGS. 19 to 21 are schematic perspective representations that illustrate a device and method for implanting medical devices in a patient's body in accordance with an eighth embodiment of the invention, wherein FIG. 19 shows an ostium plug with a lumen and magnetic implanting device, FIG. 20 shows the ostium plug in FIG. 19 in combination with a magnetically secured end plate that prevents passage of fluids through a lumen in the plug, and FIG. 21 shows an alternate magnetically secured blocking member held in place magnetically on the plug.

DETAILED DESCRIPTION OF THE PREFERRED EMBODIMENTS

Trocar Assembly with Magnetic Cap and Lumen Seal

Figure 1:
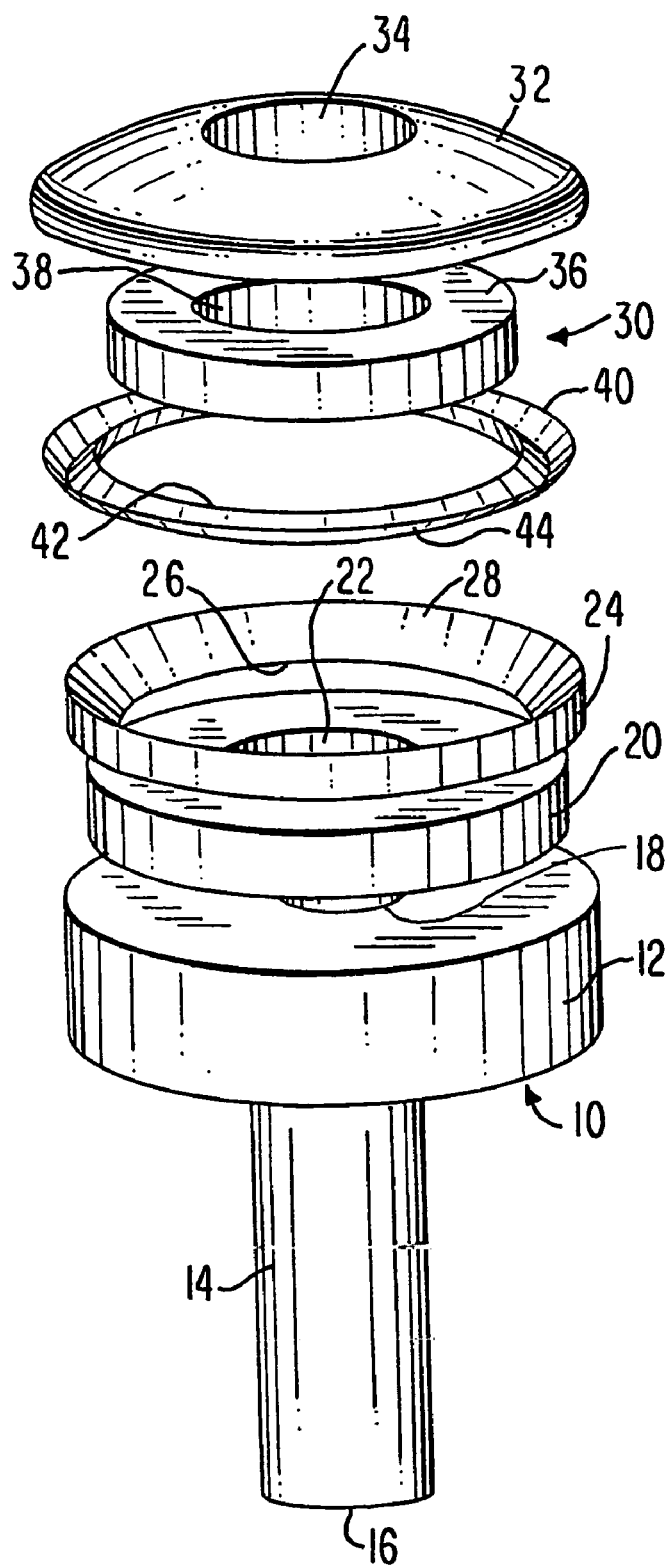
FIG. 1 is an exploded perspective schematic representation of a trocar assembly in accordance with a first embodiment of the present invention, with a trocar cap that is secured magnetically to the trocar.
Figure 2:
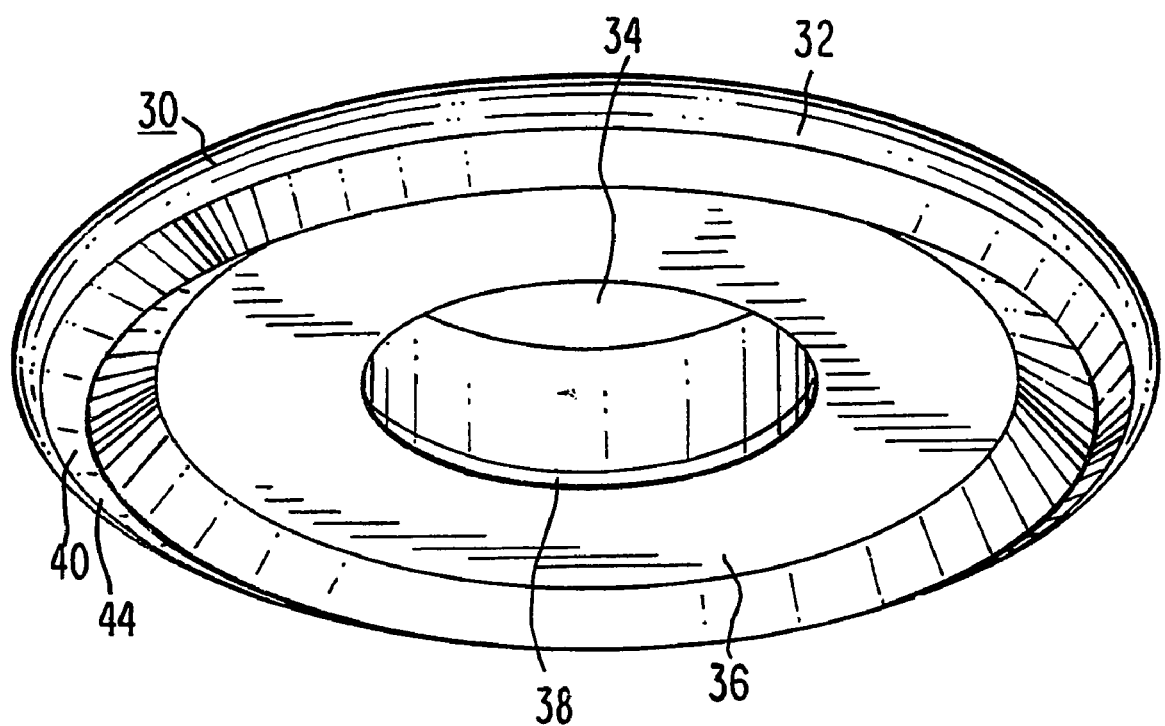
FIG. 2 is a perspective view of a trocar cap that comprises a part of the trocar assembly shown in FIG. 1.
Figure 3:
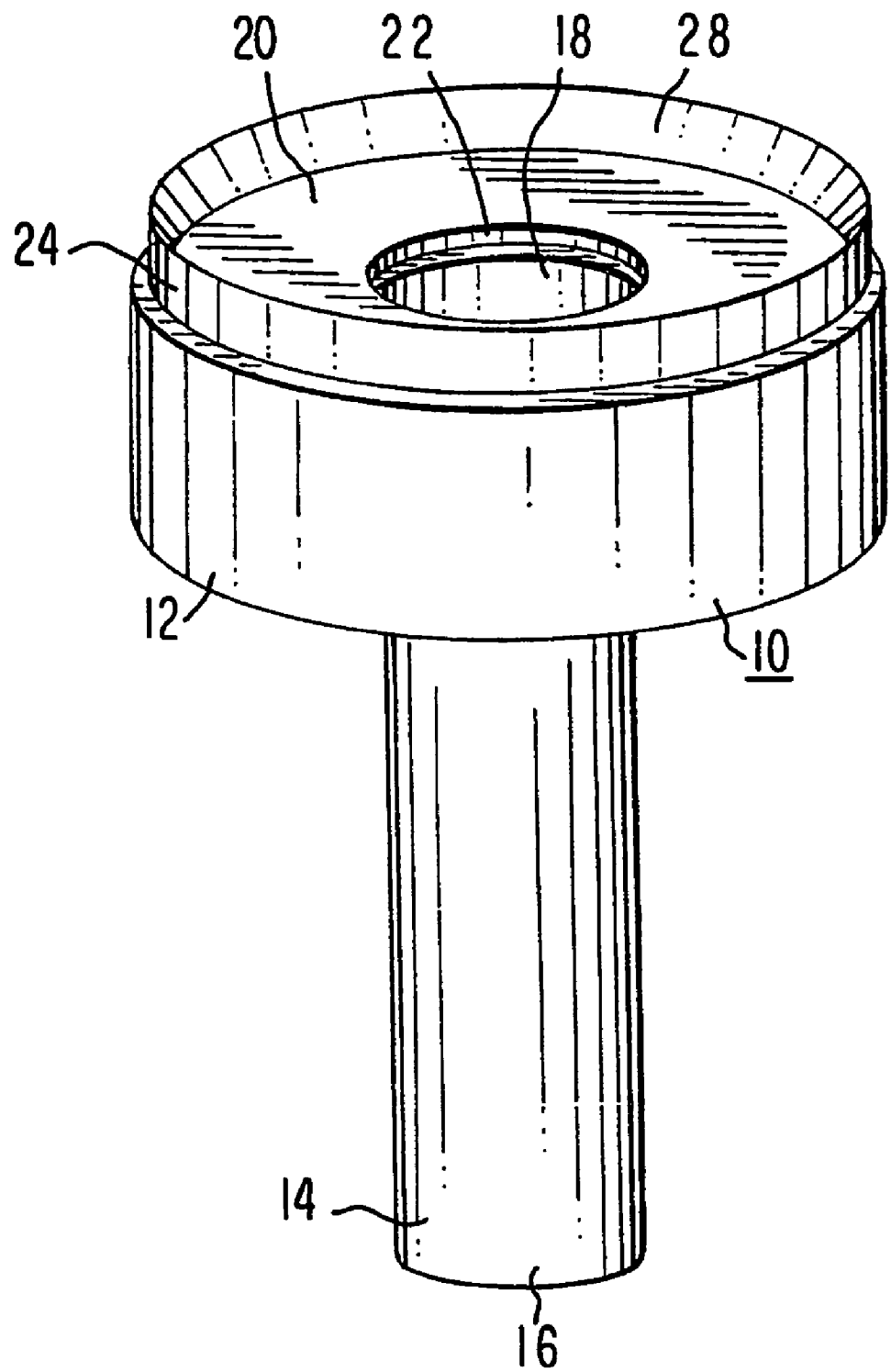
FIG. 3 is a perspective view of a trocar that comprises a part of the trocar assembly shown in FIG. 1.

FIGS. 1 to 3 are schematic depictions of a trocar assembly according to a first embodiment of the invention, with FIG. 1 being an exploded perspective view of the assembly components, FIG. 2 being a perspective view of the distal or under side of the assembled trocar cap, and FIG. 3 being a perspective view of the assembled trocar. The trocar assembly includes a trocar 10 shown in detail in FIG. 3 that comprises a base 12 with a depending, cylindrical cannula 14 terminating at a distal end 16. A trocar lumen 18 extends coaxially through the cannula from its distal end 16 and also through the base 12. As described above, the trocar 10 is used to provide access to the internal body parts of patient for a variety of minimally invasive surgical procedures. The trocar 10 further includes a flat, disc-shaped magnetic member 20 made in this embodiment of a suitable, magnetically permeable material (meaning a material that is attracted to a magnet) secured to the top or proximal side of the base 12. The magnetic disc member 20 includes a central opening 22 aligned with the lumen 18. A trocar camming ring 24 has an inside diameter 26 that permits it to fit around the outside diameter of the disc member 20 so that it can be secured directly to the proximal surface of the base 12. The trocar camming ring has a sloped inside face 28 for a purpose to be described.

The trocar assembly in accordance with this embodiment of the invention also comprises a trocar cap 30 shown in FIGS. 1 and 2. The trocar cap 30 in accordance with the present invention includes a capping member 32 with a central cap lumen 34. A flat, disc-shaped magnetic member 36, comprising in this embodiment a permanent magnet, is secured to the bottom or distal side of the capping member 32. The disc magnet 36 has a central opening 38 aligned with the cap lumen 34. The opening in the magnet 36 is typically circular with a diameter at least as large as, or possibly larger than, the diameter of the cap lumen 34. This enables easy passage of surgical instruments through the trocar lumen 18 and the cap lumen 34. A cap camming ring 40 has an inside diameter 42 that permits it to fit around the outside diameter of the magnet 36 and be secured directly to the underside of the capping member 32. The cap camming ring 40 has a sloped outside face 44 and is dimensioned so that the sloped faces 28 and 44 of the trocar and cap camming rings 24 and 40 mate when trocar cap is in place on the trocar.

In use, the cannula 14 extends through an incision and the underside of the base 12 rests against the patient's skin, with the distal end 16 of the cannula disposed within a body cavity of the patient. As is conventional, this permits the passage of instruments used in the surgical procedure and the removal of tissue from the patient. In addition, insufflation gases can be introduced through the lumen 18 in the conventional manner. The trocar assembly of the present invention also facilitates many of the manipulations required during the minimally invasive surgical techniques associated with the use of this type of trocar, in ways not provided by prior art arrangements, as described further below.

An important feature of this aspect of the invention is that the cap 30 is held in place on the trocar 10 by the magnetic attraction of the magnetically permeable member 20 on the trocar base 12 and the magnet 36 on the capping member 34. Those skilled in the art will appreciate that the magnetically permeable member could be mounted on the trocar base and the magnet could be mounted on the capping member without affecting the operation of this aspect of the invention. It will also be appreciated that any suitable materials can be used for the magnetically permeable member and the magnet. Examples of materials suitable for the permanent magnet component of the invention are neodymium-iron-boron (NeFeB), samarium cobalt (SmCo), and alnico (AlNiCo). NeFeB and SmCo are rare-earth magnets and are preferred because they provide a very strong magnetic force. SmCo is slightly preferred because it is more resistant to corrosion than NeFeB. Alnico can be cast or sintered and therefore can be made into different shapes more readily. Hard ferrite or ceramic magnets, made from a combination of either barium or strontium oxide and iron oxide can also be used. The magnetically permeable material component of the invention can be a material such as cold-rolled steel or an iron-cobalt alloy (with 50% iron-50% cobalt), to name two possible materials known in the prior art. It may also be desirable to encase the permeable magnetic material and/or the magnet in a corrosion-resistant, biocompatible material. While the trocar and cap may be designed to be disposable, the encasing material can also be chosen so that it can be repeatedly cleaned and sterilized.

As a result of their mutual magnetic attraction, the cap 30 will readily attach to the trocar 10 as soon as the cap is brought into proximity with the trocar base. The cap lumen 34 and trocar lumen 22 will line up axially due principally to mating of the sloped surfaces 28 and 44 of the camming rings 24 and 40, which nest with each other to positively retain the cap 30 in relation to the trocar 10 with their respective lumens in alignment.

An alternate arrangement uses two permanent magnets as the magnetic members 20 and 36. They can be magnetized with their magnetic fields oriented such that the cap 30 will only be attracted to the trocar 10 when the cap is right-side up. This will prevent operating room personnel from placing the cap upside down on the trocar in the low light of an operating room, where several activities may be underway at the same time during any given procedure, thus sometimes leading to errors of such nature that interrupt the procedure. The automatic orientation of the cap in accordance with this aspect of the invention means that the surgeon or an assistant does not have to look away from a video monitor in the operating room just to ensure proper placement of the reducer cap on the trocar.

Removal of the cap 30 is easily accomplished by the surgeon exerting a sideways, radial force on it with a finger or thumb, to cause the camming rings' sloping faces 28 and 44 to effect axial separation of the magnetic members, thus allowing the surgeon to grasp the edge of the capping member 32 and remove the cap 30 from the trocar 10. Thus, the cap is readily manipulated, even in low-light situations, by the surgeon or by other operating room personnel if the surgeon's hands are otherwise occupied. It also avoids the exertion of an excessive amount of axial force on the trocar to effect cap removal, which could cause the trocar to be displaced with consequent loss of insufflation. The cap can be tethered to the trocar base by any suitable means, such as a monofilament thread (not shown), to prevent the cap from being misplaced while it is not in position on the trocar base.

In addition, the camming rings 24 and 40, or one of them, may be made of or coated with a compliant material such as silicone rubber that will create a seal between the cooperating sloped faces 28 and 44, which will even more positively seal the trocar lumen 18. Of course, the hardness of the compliant material will have to be compatible with the camming function performed by the rings. That is, the sloped faces must have a coefficient of friction that will permit ready separation of the magnet/magnetic material when the cap 30 is moved sideways, as described above. This can be facilitated if the camming rings 24 and 40 are dimensioned to maintain a space between the magnet members when the cap 30 is in place on the trocar 10. Of course, if the magnetic members are coated, as described above, they will inherently not be in direct contact with each other, and further spacing may not be desired. Nevertheless, the structure of the present embodiment permits a large choice of configurations and materials adapted to particular applications.

Those skilled in the art will appreciate that other details of this embodiment may be further adapted to particular uses and fabrication methods. For example, the capping member 32 may be made inexpensively by molding of a suitable plastic material. In addition, the camming member 40 may be integrally molded with the capping member 32. The trocar base 12 (and the camming member 20) may also be made by molding a suitable plastic material. An advantage of molding is that it permits the capping member 32 and trocar base 12 to assume a wide variety of configurations to suit particular surgical applications. This is important because the cap and trocar can assume myriad different forms, as is seen in the prior art patent documents referred to above. In that regard, it will be appreciated that the depiction in FIGS. 1 to 3 is intended to be schematic for the purposes of explaining the invention and its advantages, not to suggest a particular form for the trocar 10 and cap 30.

The present invention also provides another advantage relating to ease of manipulation during a surgical procedure. The disc magnet 36 surrounding the cap lumen 34 creates an axisymmetric magnetic field aligned with the cap lumen 34 that can be used to advantage by employing a surgical instrument with a non-magnetized magnetically permeable member at least at its tip. A surgical instrument is not shown in FIGS. 1 to 3, but it can be visualized by referring to instrument I shown in FIGS. 12 to 14, which show a surgical instrument of the type used in the procedures discussed herein and can be provided with a distal tip region incorporating a magnetically permeable member (for example, the instrument end effector or a retrofitted member). The magnet in the cap generates a sufficiently strong magnetic field to cause the distal end instrument to be held securely in line with the cap lumen 34 when the instrument is brought into proximity with the cap 30, thus permitting the instrument to be easily and readily inserted into the cap lumen 34 without undue manual manipulation. This is particularly advantageous because most instruments used in minimally invasive procedures such as those employing a trocar are very elongated and can be awkward to manipulate when outside the body, which in turn can make it difficult to introduce the instrument tip into a small cap lumen. However, with a magnetically permeable tip on the instrument and a permanent magnet in the cap 30, the instrument automatically orients itself with the axis of the lumen, and is securely held in that orientation, to facilitate insertion of the instrument into and through the trocar. The strength of the magnetic field required to align the surgical instrument will depend on the magnetically permeable material used in the surgical instrument, the inherent flexibility of the instrument, the size of the cap, and similar variables. Those skilled in the art will be able to readily determine the strength of the magnetic field required for any given application.

Figure 4:
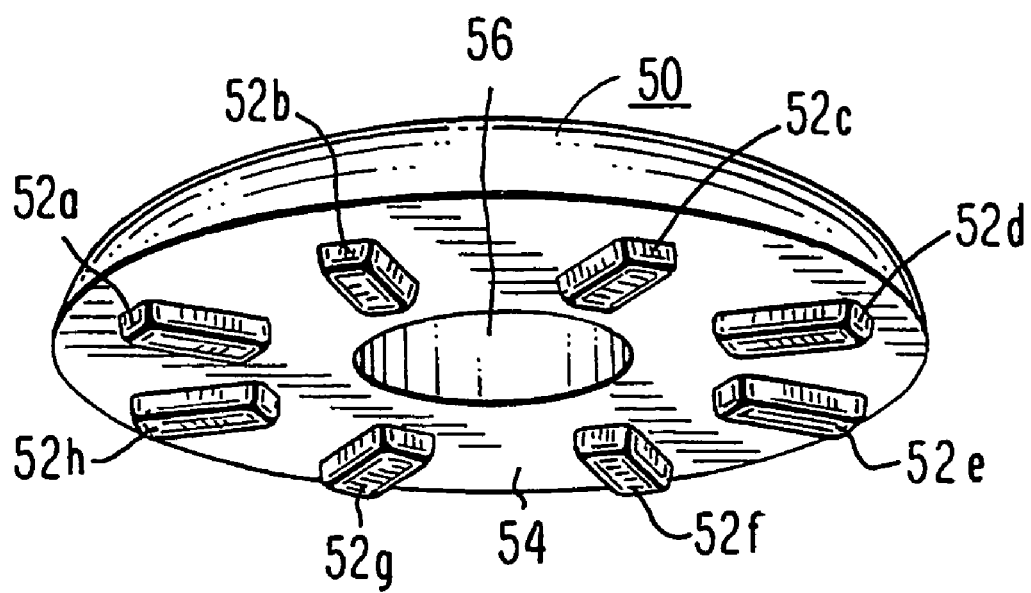
FIG. 4 is a perspective view of a distal side of an alternate embodiment of the trocar cap depicted in FIG. 2.
Figure 5:
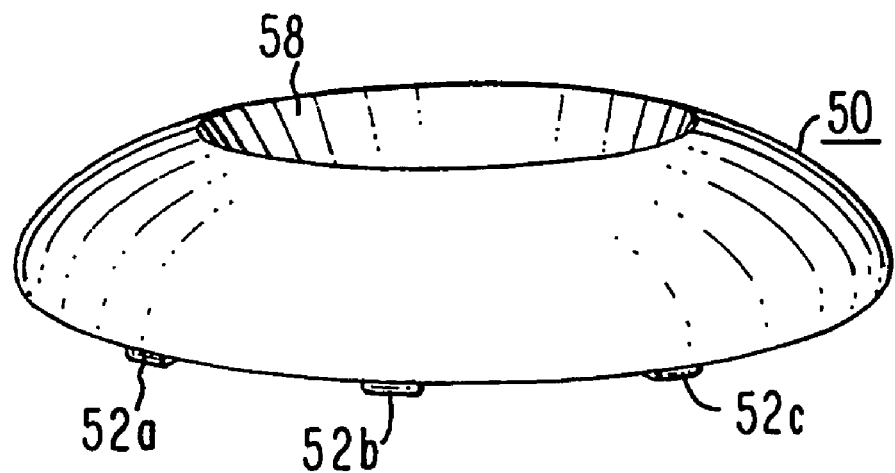
FIG. 5 is a perspective view of a proximal side of the trocar cap depicted in FIG. 4.

FIGS. 4 and 5 illustrate a trocar cap 50 in accordance with a modified version of this embodiment of the invention. It has two features that can be incorporated independently into the trocar cap of the invention. Initially, it should be understood that the trocar cap 50 is used in a fashion similar to the trocar cap 30 and also cooperates with the trocar 10 in the same manner. One of the differences in the cap 50 is that the disc-shaped magnetic member 36 is replaced with a plurality of discrete magnetic members 52a, 52b, 52c, 52d, 52e, 52f, 52g and 52h. In this embodiment, the magnetic members 52 are slightly elongated and arranged like the spokes of a wheel on the distal or underside of the capping member 54. (The camming ring is omitted from FIGS. 4 and 5 to permit a clearer view of the members 52.) The use of plural, discrete magnetic members such as those shown in FIGS. 4 and 5, or variations thereof, enables the strength and orientation of the magnetic field to be tailored to specific applications or configurations. For example, the trocar base may be constructed with discrete receptacles for the magnetic members 52 to orient the cap circumferentially in a desired manner. Or if the magnetic members are magnets, the use of discrete magnets can permit the strength of the magnetic field to be more easily chosen to cooperate as desired with the end effector of a surgical instrument with a certain ferric content.

The second feature distinguishing the cap 50 from the cap 30 is the configuration of the cap lumen. The cap lumen 56 in this embodiment has a funnel-shaped opening or mouth 58 at its proximal side. This assists in the introduction of the surgical instrument into the lumen, because it does not require the alignment to be as precise as would be required if the lumen opening were the same size as the remainder of the lumen. It will be readily apparent that providing a funnel-shaped opening 58 is particularly advantageous when the cap incorporates a disc-shaped magnet like the magnet 20 shown in FIGS. 1 and 3, for the reasons described above. That is, the magnet will assist in the alignment of the instrument at the mouth of the lumen, but avoids the necessity of achieving precise alignment to introduce the instrument into the lumen. In addition, the structure of the cap forming the funnel-shaped opening can be a magnet, which will even more positively position the surgical instrument for introduction into the cap lumen 34' and trocar lumen (not shown).

The alignment feature is a significant aspect of the present invention, and numerous adaptations thereof are possible. For example, it can be used in a trocar that does not normally use a reducer cap. That is, it was noted above that the magnetic member 20 in the trocar shown in FIGS. 1 and 3 could be a permanent magnet. Trocars with lumen valves are sometimes used without reducer caps, but if the trocar includes a magnetized magnetic member 20 that produces a magnetic field of sufficient strength, it will serve the same instrument alignment function as the magnet 36 surrounding the cap lumen. In addition, the proximal end of the trocar lumen could be funnel-shaped, like the cap opening 56 depicted in FIG. 5, to enhance the alignment function of the trocar magnet even further as discussed in connection with FIG. 5. Moreover, the alignment aspect of the invention can be incorporated into a reducer cap that attaches to a trocar in conventional fashion (that is, non-magnetically). In other words, a trocar cap could include magnets oriented around a lumen as in the above discussed embodiments to align a surgical instrument with the cap lumen, but which nevertheless attaches to the trocar like a conventional cap, such as that shown in U.S. Pat. No. 5,338,307, for example. All of those variations are within the scope of the present invention.

Lumen Valve Enhancements

Figure 6:
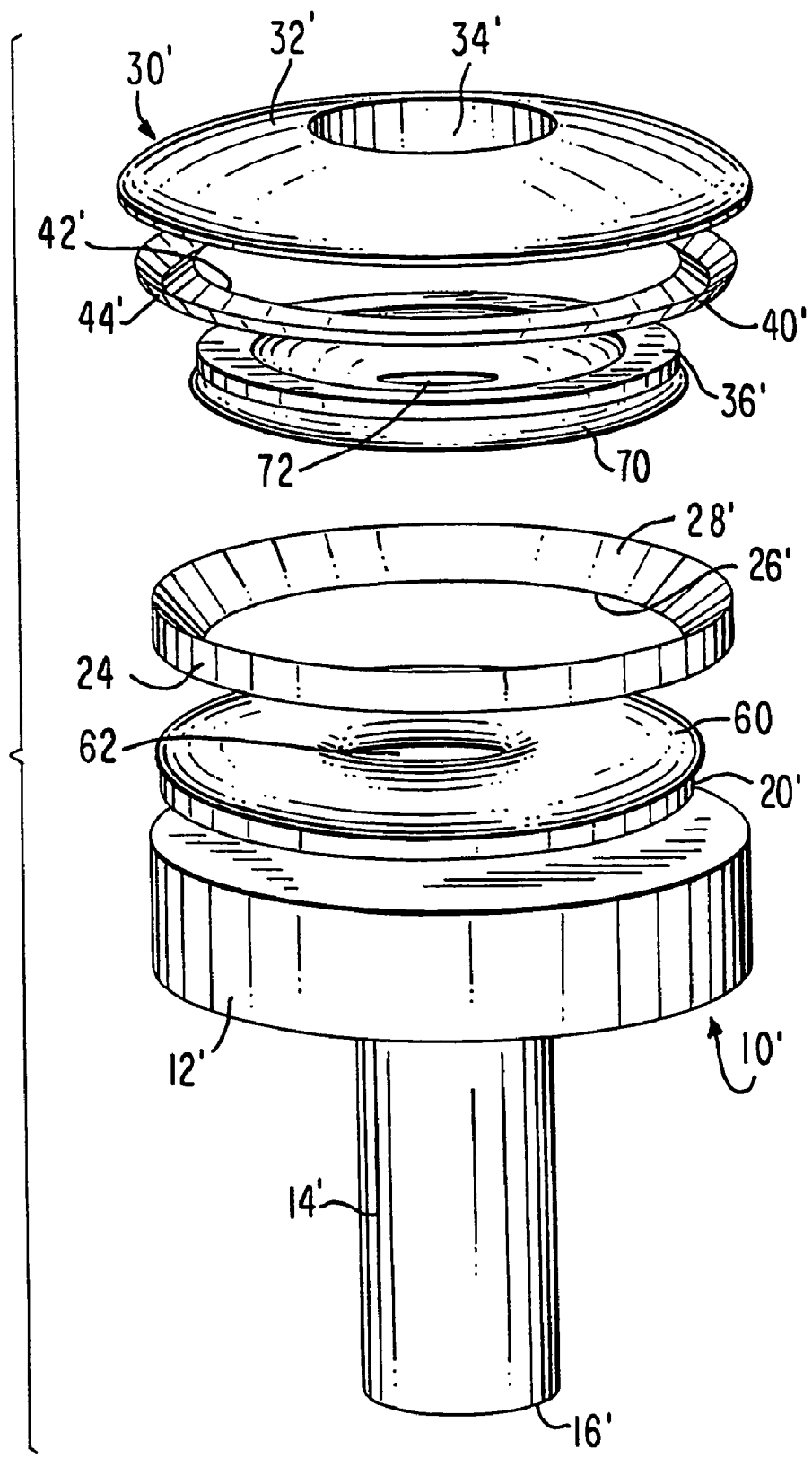
FIG. 6 is an exploded perspective schematic representation of a trocar assembly with a lumen valve operable through the magnetic attraction of the cap and trocar, in accordance with a second embodiment of the present invention.
Figure 7:
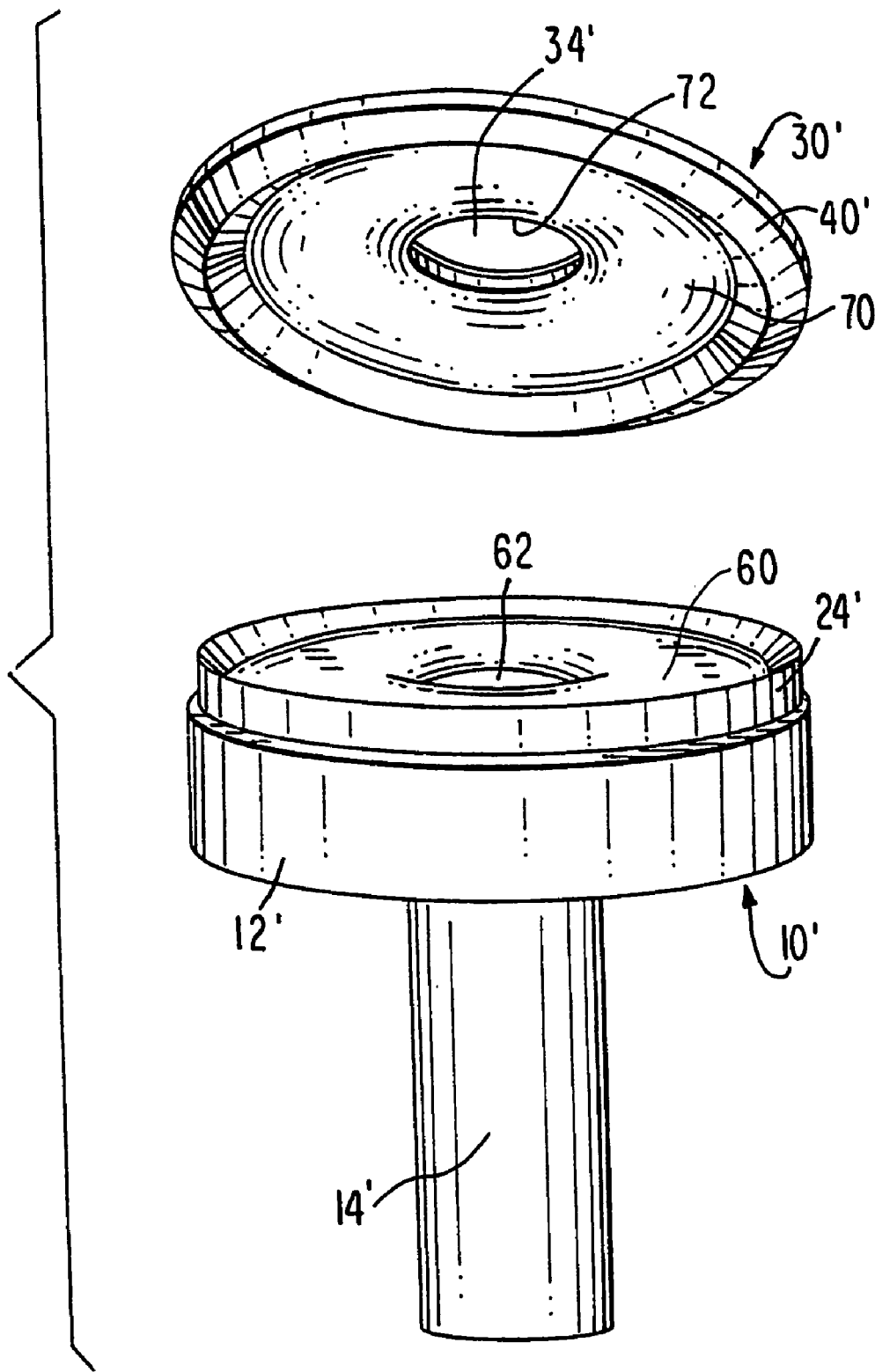
FIG. 7 is a perspective schematic representation of the assembled trocar cap and trocar comprising the trocar assembly shown in FIG. 6.

Another embodiment of the invention, depicted in FIGS. 6 and 7, takes further advantage of the presence of the magnetic members to provide an improved lumen seal for the surgical instrument. In FIGS. 6 and 7 parts corresponding to those in the embodiment described above in connection with FIGS. 1 to 3 bear the same reference numerals, with an added prime (') notation. The embodiment depicted in the perspective views of FIGS. 6 and 7 include a two-component lumen seal that forms a seal around a surgical instrument (not shown) inserted through the cap lumen 34' and trocar lumen (not shown).

Referring first to FIG. 6, one component of the lumen seal of this embodiment is a trocar lumen seal 60, which comprises a toroidal body of compliant material such as an elastomeric rubber or silicone material. Alternatively, it can be hollow and filled with a sterile saline solution, hydrogel, or other biocompatible fluid medium. It is mounted to the trocar 10' on the proximal face of the magnetic member 20' with its central opening 62 in line with the cap lumen 34'. The other component of the lumen seal is a similar toroidal body 70 secured to the distal face of the magnetic member 36' in the cap 30'. The toroidal body 70 is disposed with its central opening 72 aligned with the cap lumen. When the cap 30' is in place on the trocar 10', the magnetic attraction between the magnetic members axially compresses the two toroidal bodies 60 and 70, which causes them to expand radially inwardly. As can perhaps be appreciated more readily from FIG. 7, the radial expansion closes the openings 62 and 72, sealing the cap and trocar lumens.

However, when a surgical instrument is to be passed through the cap and trocar lumens, the compliant material of the lumen seal components 60 and 70 yields and permits sufficient enlargement of the openings 62 and 72 to allow passage of the instrument while sealing around the instrument shaft. Those skilled in the art will appreciate that the properties of the material used for the components of the lumen seal and the magnetic attractive force exerted by the magnetic members can be selected through experimentation to accommodate the different sizes of surgical instruments to be used. The goal is to provide sufficient sealing around the instrument, while still permitting it to be moved axially through the lumen. Otherwise, the construction and operation of the trocar/cap combination of the present embodiment is the same as described in connection with the embodiment depicted in FIGS. 1 to 5. A lumen valve arrangement according to this embodiment of the invention provides a low profile trocar, thus avoiding potential stability problems as discussed above, while still providing an effective lumen seal.

It will be further appreciated that other lumen seal configurations can be used with the embodiment depicted in FIGS. 1 to 5. For example, a more conventional type lumen seal can be incorporated into the base 12 of the trocar 10. For example, if the magnetic member 20 in the trocar base is a magnet, it can be employed in adaptations of magnetic valves like those shown in prior art patent documents such as the above-mentioned U.S. Pat. Nos. 4,535,773, U.S. Pat. No. 5,423,761, German Patent Publ. No. 28 00 607, Japanese Patent Abstract No. 2000/000246, and International Appln. No. WO01/43812. Accordingly, the descriptions of the magnetic valve arrangements in those patents are incorporated by reference herein. The presence of a magnet in the trocar base of the present invention permits those magnetic lumen valve configurations to be incorporated into the trocar in those instances when trocar stability is not as critical.

Another lumen valve arrangement that can advantageously be incorporated into a trocar assembly in accordance with the present invention is depicted schematically in FIGS. 8a to 8c. In this embodiment, the trocar base 12 shown in FIGS. 1 and 3, for example, comprises a hemispherical permanent magnet 112, shown in FIGS. 8a and 8b, with a depression 118 that forms a portion of a concentric sphere. As with the trocar 10 shown in FIGS. 1 and 3, a cannula depends from the base 112, but it is not shown in FIGS. 8a and 8b. Likewise, a lumen extends axially through the cannula in alignment with the center of the hemispherical magnet and thence through the center of the spherical portion that forms the depression 118. The cap in the trocar assembly of this embodiment comprises the spherical magnet 130, depicted in FIG. 8a, with a lumen 134 extends through the center of the sphere. The polarities of the trocar magnet 112 and the cap magnet 130 are shown in FIGS. 8a to 8c. The polar axis of the trocar magnet 112 is aligned with the axis of the trocar lumen and the polar axis of the cap magnet 130 is perpendicular to the axis of the cap lumen 134.

In use, the lumen 134 of the cap magnet shown in FIG. 8a is placed on a surgical instrument S near the end thereof. This permits the instrument to be introduced into the trocar lumen with the spherical cap 130 nesting in the spherical depression 118 in the trocar magnet 112 and the instrument S extending into the trocar, as seen in FIG. 8a. The depression 118 in the trocar magnet assists in guiding the surgical instrument into the trocar lumen, and as soon as the magnets 130 and 112 are in sufficient proximity, the cap 130 positively "snaps" into place in the depression 118 due to the magnetic force between them, as in the embodiments discussed above. The surgical instrument S can then be extended into the patient to effect the surgical procedure being performed. When the surgical instrument S is withdrawn from the patient, the cap magnet 130 stays in place in the depression 118. When the instrument is fully withdrawn, as in FIG. 8b, the orientation of the magnetic polarities of the two magnets 112 and 130 causes the cap magnet 130 to rotate 90° into the position shown, thus sealing the trocar lumen. It will be appreciated that the depression and the valve member do not have to be spherical. They in fact can be any body of rotation, as long as they have mating surfaces that can slide relative to each other. For example, the depression could be elliptical with a major axis of rotation perpendicular to the lumen axis and the valve member could be an elliptical solid body of rotation with the lumen extending along a minor axis of rotation.

The magnets used in this embodiment may be made of suitable materials, with or without coatings, as discussed above. It may also be desirable to cover the cap magnet 130 and line the depression 118 with an anti-friction surface such as a Teflon® polytetrafluoroethylene coating to facilitate rotation of the cap magnet in the depression. The highly schematic nature of the illustration in FIGS. 8a to 8c will also be appreciated. For example, the magnet 112 can be incorporated into known trocar base structures, and need not comprise the trocar base itself. In addition, this embodiment of the invention is not restricted to a trocar assembly having the magnet 112 in a trocar. That is, the magnet 112 could be included as part of a trocar cap, instead of the trocar base. Such a cap could either attach to the trocar magnetically, as in previously described embodiments, or attach to the trocar in an alternate manner, but still incorporate a magnetic valve arrangement in accordance with this embodiment. In this respect, this embodiment of the invention can be understood in its broad aspects to comprise a magnetic valve body 112 having a lumen, within which rotates a magnetic valve member 130 also having a lumen to open or close the valve.

Other modifications are also applicable to this embodiment. For example, although it is advantageous in many circumstances to polarize the magnets 112 and 130 so that the valve member 130 closes when the instrument S is not present, the polarities of the magnets can be oriented differently so that the lumen 134 in the valve member 130 aligns with the lumen in the valve body 112 when the instrument is not in place. In that case, the valve member will be provided with a mechanism by which to close the valve manually to seal the trocar (Oust as would be needed to open the valve manually in the first construction). Accordingly, the valve of this embodiment may be constructed to be either preferentially open or closed when a surgical instrument is not in place. That preference can be chosen depending on the application in which the valve is to be used. A principal advantage to this valve mechanism in either construction is that during operation of the valve between its open and closed positions, the overall profile of the valve remains unchanged, thus eliminating the need to provide sufficient space for movement of a valve member, as in prior art valves like those shown in U.S. Pat. No. 4,535,773, U.S. Pat. No. 5,423,761, French Patent No. 2,719,210, German Patent Publ. No. 28 00 607, Japanese Patent Abstract No. 2000/000246, and International Appln. No. WO01/43812, for example.

Finally with regard to this embodiment, it may be more advantageous to have the axis of magnetic polarity of the valve member 130 at an oblique angle to the axis of the lumen 134, rather that perpendicular to it as depicted in FIG. 8c. Having the magnetic polarity at an oblique angle may provide a stronger attraction and better seating of the valve member 130 into the depression 118 in the valve body 112. One skilled in the art will be able to determine from the intended use of the device the best angle between the axis of magnetic polarity of the valve member 130 and the axis of the lumen 134.

Mini-Trocars Embodying the Invention

FIGS. 9 and 10 illustrate in its simplest form another embodiment of the invention in which magnetic coupling enables the size of the trocar to be substantially reduced for surgical procedures using instruments of reduced size, on the order of 1-3 mm in diameter. These "mini-trocars" are typically used for introducing smaller size instruments to a surgical site and need not provide for the removal of tissue samples through the trocar. Since the resulting small diameter of the cannula lumen usually inhibits the loss of insufflation gases, these trocars do not necessarily need an internal valve. Thus, they can be made with a low profile, which makes them very stable when in place in a patient. However, in mini-laparoscopic procedures, or other procedures in which such small instruments are to be inserted through a cannula, it can be even more difficult to align the instrument with the trocar lumen. This embodiment of the invention addresses that difficulty.

An embodiment of a mini-trocar assembly in accordance with this embodiment comprises a trocar 210 with a base 212 and a cannula 214, having a lumen 218 that extends axially through the trocar to its distal end 216. The trocar base 212 is on the order of about 10-20 mm in diameter and is about 8-15 mm wide in the axial direction, and thus is small enough to avoid stability problems associated with larger trocars. The lumen 218 is also correspondingly small, which presents very little cross-sectional area for the escape of insufflation gases. The cannula 214 is about 2-5 mm in diameter, and is long enough to extend to a depth sufficient to enable the relevant procedure to be performed. As noted above, elaborate lumen sealing mechanisms, such as those incorporated in larger trocars, are not required. However, it is still preferable to seal the trocar lumen when the surgical instrument is removed.

To that end, the trocar base 212 includes a magnetic member corresponding to the magnetic member 20 in the embodiment depicted in FIGS. 1 to 3. This magnetic member may either comprise the base 212 itself, or be a separate component disposed internally of the base. The cap 230 also includes a magnetic member corresponding to the magnetic member 36 in FIGS. 1 to 3. Both the trocar magnetic member and the cap magnetic member can be made of a materials as discussed above in connection with the embodiment of FIGS. 1 to 3, and coated or otherwise embedded in protective materials as discussed above. To ensure proper placement of the cap 230 on the trocar base 212, the trocar base includes a shoulder 228, which forms in the proximal end of the base a recess dimensioned slightly larger than the dimensions of the cap. If desired, the rims 244 of the disc-shaped cap can be beveled to cooperate with a beveled edge on the shoulder 228, thus providing a camming action to separate the cap 230 from the base 212 by exerting a lateral force on the cap. Both edges of the cap are beveled so that the camming action is available regardless of which side of the cap is in contact with the base. The cap can be tethered to the trocar base as discussed above, to prevent the cap from being misplaced while it is not in position on the trocar base.

In a preferred construction, the trocar base 212 either is a magnet, or has a magnet internally thereof, in a configuration that creates an axially extending magnetic field in the manner discussed above in connection with FIGS. 1 to 5. If the surgical instrument has a magnetically permeable end effector and the magnetic field generated by the magnet in the trocar base has the necessary predetermined strength, the instrument will be aligned and guided into the trocar lumen in the manner discussed above. As discussed above, the proximal opening of the trocar lumen can be funnel-shaped, thus further facilitating introduction of the instrument into the trocar lumen.

FIG. 11 illustrates an alternate version of this embodiment of the invention. In this figure, parts corresponding to those in the embodiment shown in FIGS. 9 and 10 bear the same reference numerals, with an added prime (') notation. In this embodiment, the cap 230' is a spherical magnet, and the trocar base 212' has a recess forming a part of a sphere with the same diameter as the spherical cap 230'. This configuration facilitates handling of the cap, since it is larger than the cap 230. It also facilitates removal since the cap has a higher profile and although it is firmly held in place when in the recess in the trocar base, it will simply roll out of the recess and be easily gripped upon exertion of a lateral force. As with all of the trocar base/cap assemblies described herein, the present invention enables the cap simply to be brought into proximity with the trocar base and released, and it will be magnetically attracted to the base to seal the trocar lumen when the instrument is not in place.

Figure 12:
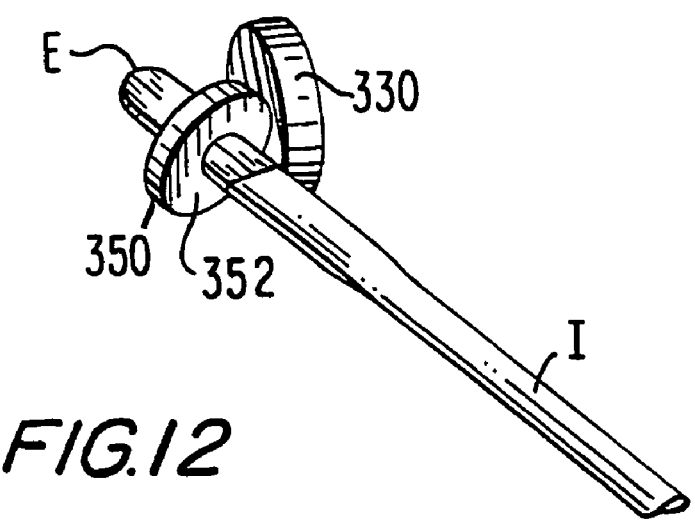
Figure 13:
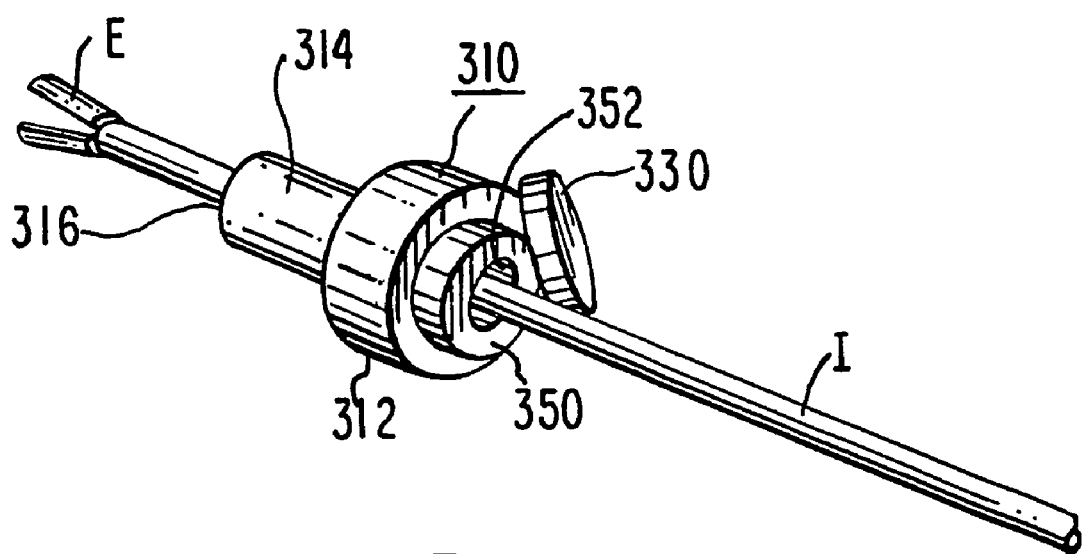
Figure 14:
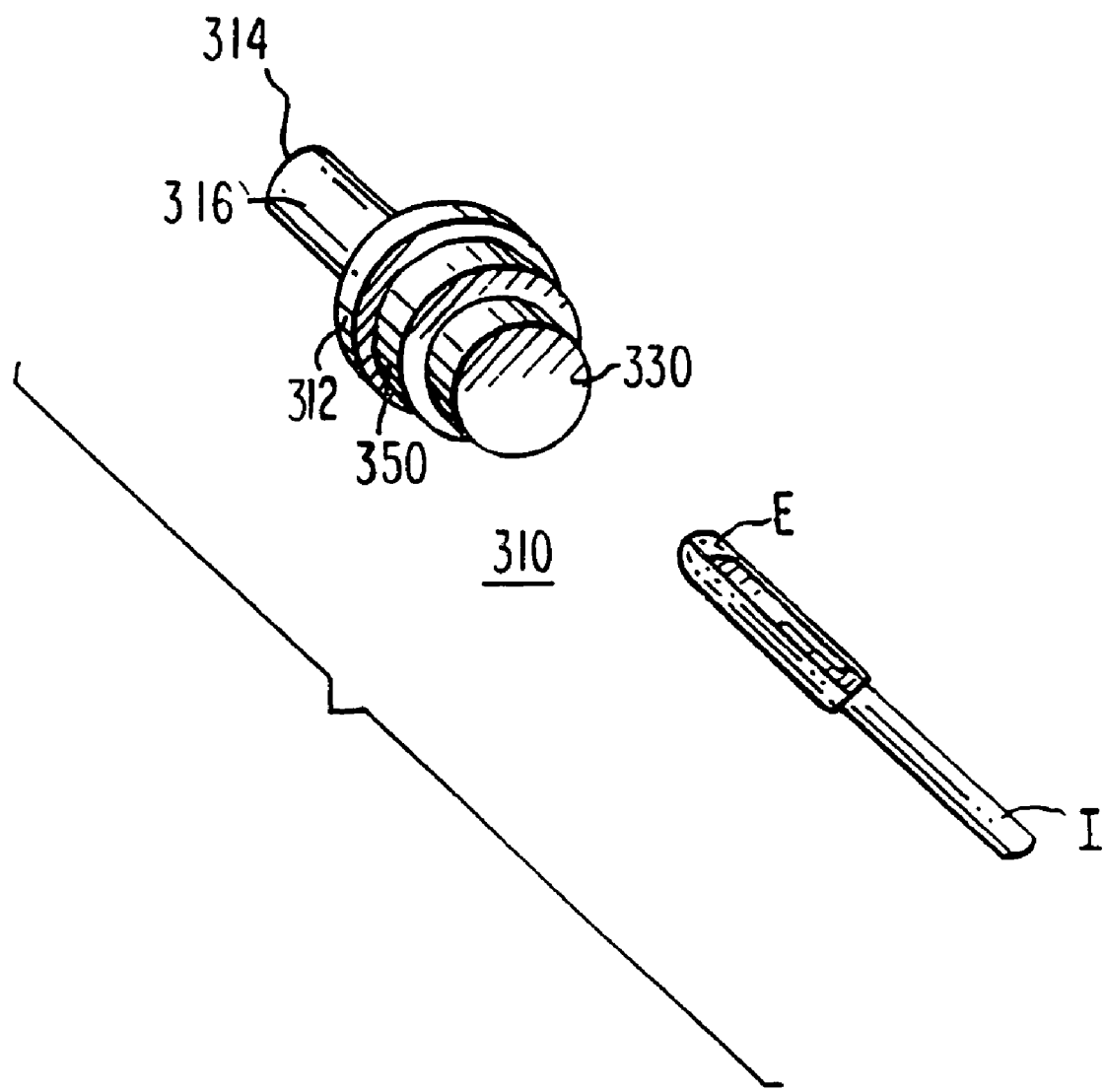

FIGS. 12 to 14 depict another application of the principles underlying the present invention particularly well adapted to surgical procedures employing mini-trocars, although those skilled in the art will appreciate that the construction shown in these figures can be used with larger trocars, as well. FIG. 12 is a schematic perspective view of the aligning/capping device and method of this embodiment. A cap 330 comprises a disc-shaped permanent magnet 330. A securing member 350 also comprises a disc-shaped permanent magnet, but includes a central lumen 352. The magnetic fields of the cap 330 and the securing member 350 are oriented such that they are attracted to each other with their axes in axial alignment. A surgical instrument I has an end effector E. The materials and constructions discussed above can be used for these components.

FIGS. 13 and 14 depict a mini-trocar 310 used with this embodiment of the invention. The trocar 310 is similar to the trocar 210 shown in FIGS. 9 to 11 and described above. It comprises a base 312 that comprises a magnetically permeable member that may either comprise the base 312 itself, or be a separate component disposed internally of the base. The trocar includes a cannula 314 terminating at a distal end 316, with a lumen (not shown) extending axially through the cannula 314 and the base 312 from the distal end of the cannula to the proximal end of the base.

To effect the aligning/sealing method comprising this embodiment of the invention, the surgical instrument end effector E is passed through the lumen 352 of the securing disc magnet 350. The sealing disc 330 is then positioned in proximity to the magnet 350 so that the magnet attraction between them forces the instrument I against the wall of the lumen 352. This effectively connects the instrument I and the two magnets and secures them in place with the end effector E protruding from the securing member 350. It will be appreciated by those skilled in the art that it is not necessary to have a magnetically permeable end effector E on the instrument I, since the magnetic attraction between the securing and sealing members will effectively cause the securing member to grip the shaft of the instrument by friction.

The end effector E is automatically aligned with the entrance of the trocar lumen by the magnetic attraction between the disc magnet 350 and the trocar base 312, with minimal visual effort required by the surgeon and/or other operator. That is, the alignment aspect of the invention is effected in the manner discussed above in connection with other embodiments. Once the end effector E with the magnet 350 in place is within proximity of the trocar base, they couple together and the end effector is presented to and aligned with the trocar lumen, and the instrument I can be fed through the trocar to position the end effector E within the patient. The end effector is then manipulated, as depicted schematically in FIG. 13, to effect the desired procedure. Meanwhile, the sealing member 330 stays attached to the securing member and/or the trocar base 312 by magnetic attraction. FIG. 14 shows the positions of the sealing member 330 and securing member 350 after withdrawal of the instrument I from the trocar 310. The sealing member 330 has assumed a position in axial alignment with the securing member 350 due to the orientations of their respective magnetic fields. This automatically seals the trocar lumen when the instrument I is withdrawn.

In a variation of the depicted construction, the trocar base 312 and the securing member 350 can be provided with cooperating sloped shoulders, as described in connection with the embodiment depicted in FIGS. 9 to 11, to permit the securing member 350 and sealing member to be more easily removed if another instrument is to be used. That instrument can have its own securing member and sealing member attached as shown in FIG. 12. In addition, more than one of the magnets 350 can be "stacked" on the instrument shaft, so that with successive uses, each individual magnet is left in place on the trocar and the next magnet will align the instrument the next time the instrument is used. Those skilled in the art will recognize other variations on the depicted construction that come within the spirit of the invention. For example, the configurations of the various members, including the trocar and securing and sealing members, are depicted in highly schematic form in FIGS. 12 to 14 for purposes of illustrating basic principles underlying this aspect of the invention. In addition, it will be appreciated that the construction and composition of the various parts components of this embodiment will be chosen to minimize the friction between the instrument and the securing member and cap as the instrument slides in and out of the trocar.

Magnetic Placement of Surgical Devices

Figure 15:
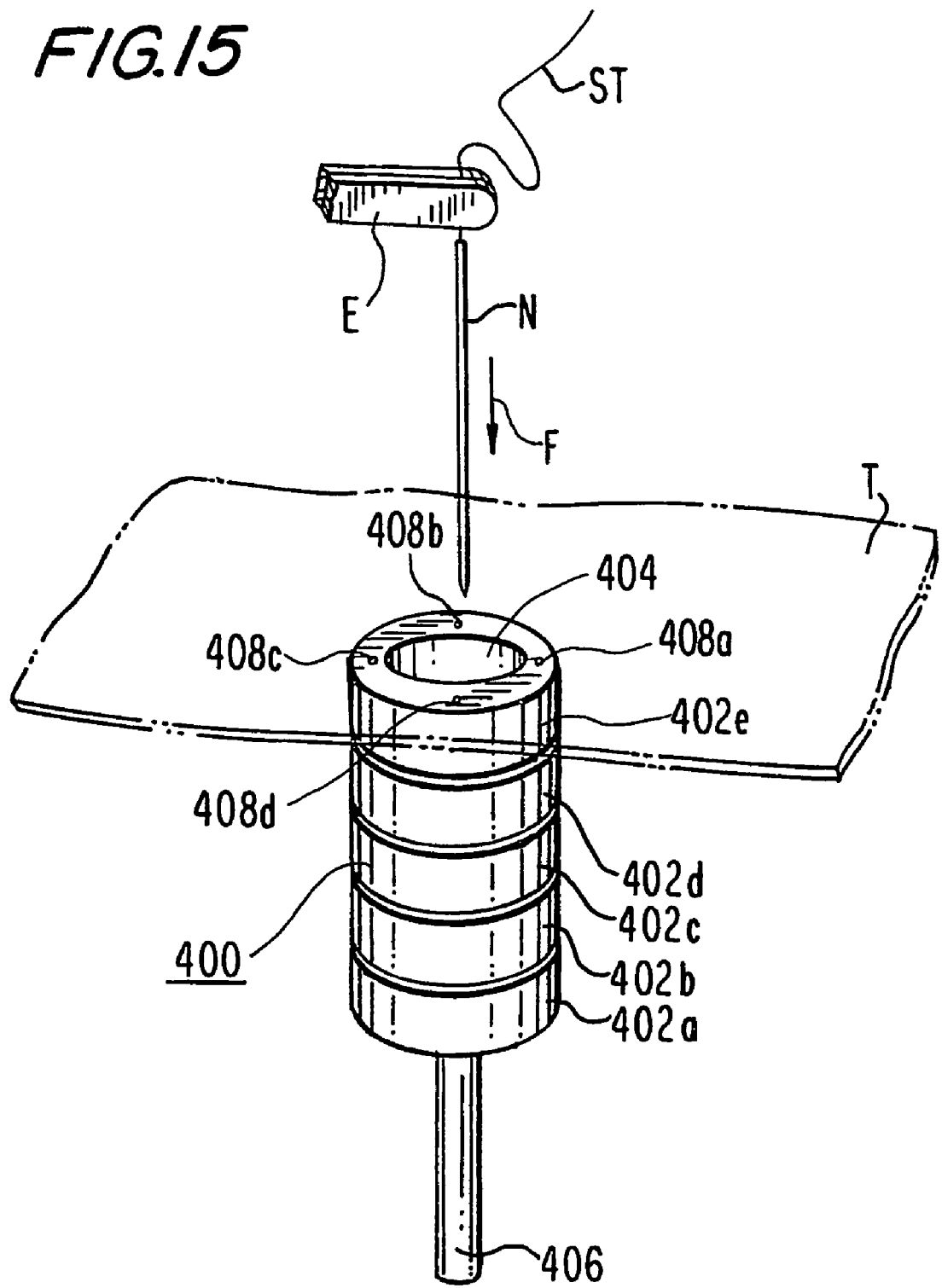
FIG. 15 is a schematic representation of a sixth embodiment of the invention in which a magnetic aligning device on one side of a tissue boundary aligns a surgical device on another side of the tissue boundary.

FIG. 15 is a perspective view of another embodiment of the invention in which a magnetic forces are employed within a body cavity for aligning surgical devices or components thereof across a tissue boundary. During minimally invasive surgical procedures, it is often necessary to precisely position, or otherwise introduce or manipulate, a surgical device across a tissue boundary. The most common instance, illustrated in FIG. 15, is the placement and aligning of a suturing needle N across an internal tissue boundary T, shown in phantom dot-dash lines in FIG. 15. In the prior art, it was necessary to grasp the needle with the end effector E of a surgical instrument and manipulate it relative to the tissue boundary. The present embodiment of the invention utilizes magnetic alignment and transillumination across the tissue boundary to facilitate placement, alignment, and capture of the needle N, which can often be of critical importance to prevent trauma to adjoining organs or tissue during suturing. This is particularly difficult in the two-dimensional field of view typically encountered in minimally invasive procedures.

A magnetic alignment device 400 in accordance with this embodiment of the invention comprises a plurality of disc-shaped magnets 410a, 402b, 402c, 402d and 402e, all of which have a central lumen and are bonded together with a suitable adhesive to form a magnetic cylinder with a central lumen 404, although the device 400 could alternatively be made in one piece. The alignment device 400 can be made of the magnetic materials discussed above and coated to enable safe use thereof, also as discussed above. The device 400 is maneuvered into place by a flexible controlling rod 406, preferably introduced into the patient through a trocar in the manner discussed above. The controlling rod may include conventional electrical wiring and a suction passage, for the purposes discussed just below. The electrical wiring connects to a plurality of LEDs (light-emitting diodes) 408*a*, 408*b*, 408*c* and 408*d* in the distal face of magnetic disc 406*e*, which can be selectively energized by controls operated by the surgeon at the proximal end of the controlling rod 406 outside the patient.

In the application illustrated in FIG. 15, the device 400 is introduced into the patient and is precisely positioned on the blind side of a tissue boundary T through which a surgical needle N is to be passed. The LEDs 408*a* to 408*d* are then energized to emit light having a wavelength and intensity chosen so that the LEDs can be seen through the tissue boundary T. With this transillumination through the tissue boundary, the surgeon is able to manipulate the device 400 into the precise position where suturing is to be performed. Optionally, the surgeon can then operate conventional controls to introduce suction through the rod 406 and the device lumen 404 and fix the device to the tissue boundary T at this location. Meanwhile, the suturing needle N is introduced into the patient through a trocar (not shown) into the patient using the end effector E of a conventional surgical instrument, such as that described above.

In the method according to this embodiment of the invention, the end effector grasps a suture ST attached to the needle N., rather than the needle itself, at a location very near to the attachment point of the suture to the needle. The needle N is made of a magnetically permeable material, so that the magnetic field created by the alignment device 400 exerts an axial force F on the needle tending to orient it axially of the device at the exact center of the lumen 404. The transillumination from the LEDs enables the surgeon to place the needle sufficiently close to the alignment device for "capture" of the needle by the magnetic field of the device at the desired target location indicated by the light. The LED illumination also provides a visual confirmation to the surgeon that the needle is properly located. The needle N, which may have punctured the tissue T by virtue of the magnetic attraction of the device 400, can then be forced all the way through the tissue boundary by urging the end effector toward the tissue boundary to push the needle therethrough. It is preferable to use a surgical instrument and end effector of non-magnetically permeable material so that the instrument and end effector are not attracted to the device 400.

It was known in the prior art to use suction to position a surgical device against an organ wall and LED illumination to indicate the location of the device from the blind side of a tissue boundary, but this embodiment of the invention provides a novel way of aligning another surgical device on the other side of the tissue boundary. As with the embodiments previously described, variations are possible within the scope of the invention. For example, the controlling rod could include a fiber optic cable to transilluminate the tissue boundary, instead of incorporating LEDs within the aligning device.

It will be appreciated by those skilled in the art that this embodiment can be easily adapted to repeatedly draw the needle N through the tissue boundary to complete an entire suturing procedure. One way to accomplish this would be to incorporate into the device 400 a grasping mechanism (not shown) to grip the needle N when it has passed through the tissue boundary T. Using a needle N that is pointed on both ends, with the suture attached in the middle of the needle rather than at one end, the first suture is performed as described above When the needle N has penetrated the tissue boundary T, the device, now gripping the needle, is used to pull the needle all the way through. The other pointed end of the needle can then be forced through the tissue boundary by the device 400, using transillumination from the LEDs to position the needle N for this next suture. The end effector E can then be used to pull the needle through the tissue boundary, with the entire process being repeated until the suturing is complete. This embodiment of the invention thus enables suturing across a tissue boundary without requiring the creation of an opening through the tissue boundary for passage of the viewing instrument to the other side of the boundary. It also alleviates some of the disadvantages of working in an area with a limited depth of field, since the magnetic alignment and capture of the needle, coupled with a lighted "target," reduces the difficulty encountered by the surgeon in manipulating a surgical needle in such an area.

Magnetic Alignment with Implanted Medication Dispenser

The embodiment of the invention to be described here is an improved construction of a device for administering medication to a patient using an implanted device. It is described in connection with a vascular access port, but it will be appreciated that the invention is not limited to that application and can be incorporated in any such implantable medication-dispensing device.

Figure 16:
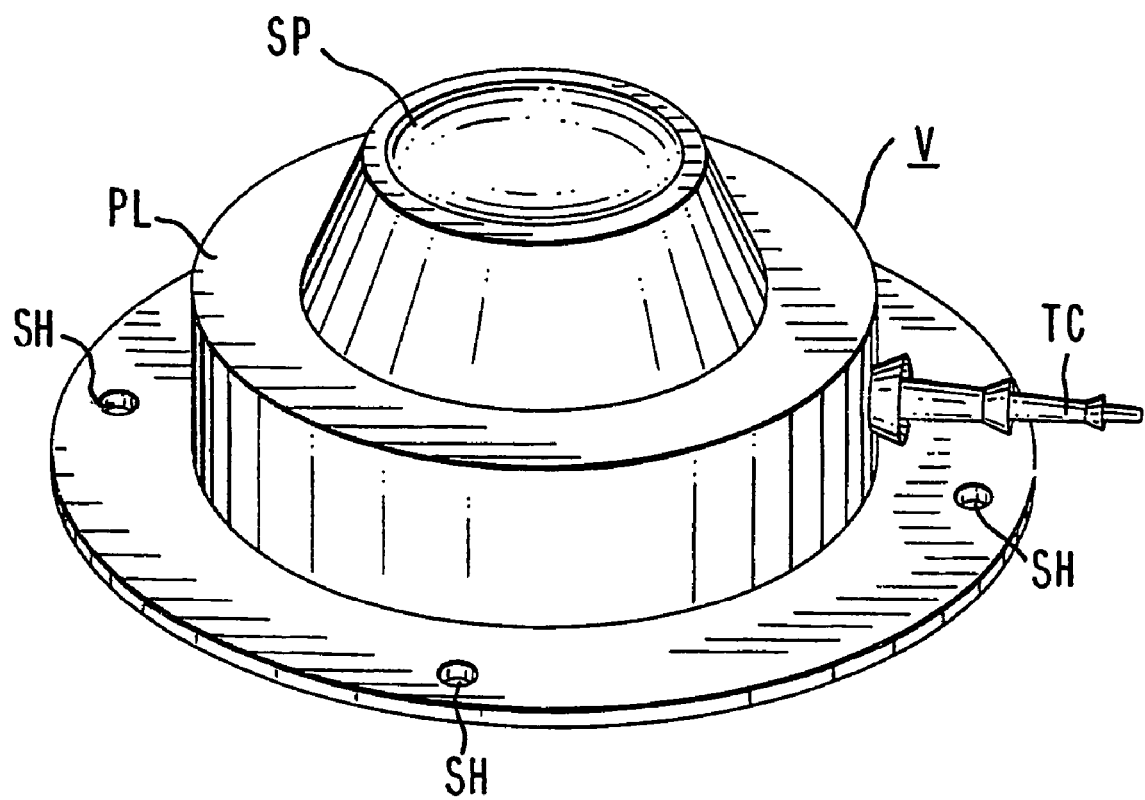
FIG. 16 is a perspective view of a prior art VAP implantable in a patient to administer medication.

Certain advantages of this aspect of the invention can be better appreciated by considering a typical prior art VAP, such as that depicted in FIG. 16. The depicted vascular access port VAP includes suture holes for securing the VAP in the patient, typically to the fascia interior of the epidermal structure. The VAP includes a plenum PL that is accessed by a septum SP, through which a needle (not shown) introduces medication into the plenum. A tubing connector TC leads from the plenum, and in use will have a tube (not shown) connected to it and, at the tube's distal end, to a vein, artery, or other anatomical structure.

Medication is introduced transdermally using any suitable administration apparatus with a needle for penetrating the septum SP and introducing medication to the plenum PL, as discussed above. If the needle is not properly aligned with the septum, the medication cannot be administered, and the needle must be withdrawn and reinserted. Repeated needle sticks can be traumatic for the patient, which is a primary reason why it is preferable to achieve medication administration on the first try. As well, certain medications may cause severe tissue reactions if injected into soft tissues rather than into an access port. This may cause inflammation, pain, tissue necrosis, and loss of function of the access port. However, another reason that has become more important in recent years is the danger posed to the individual administering the medication. Plural needle sticks can leave the patient's blood or other fluids on the needle, so that if the person administering the medication to the patient then accidentally sticks himself or herself, there is a chance of transmission from the patient of blood-borne diseases such as HIV, hepatitis, etc. The high profile of prior art VAPs reduces to some degree the chance that the first needle stick will not find the septum, but that construction can be uncomfortable and unsightly for the patient.

Figure 17:
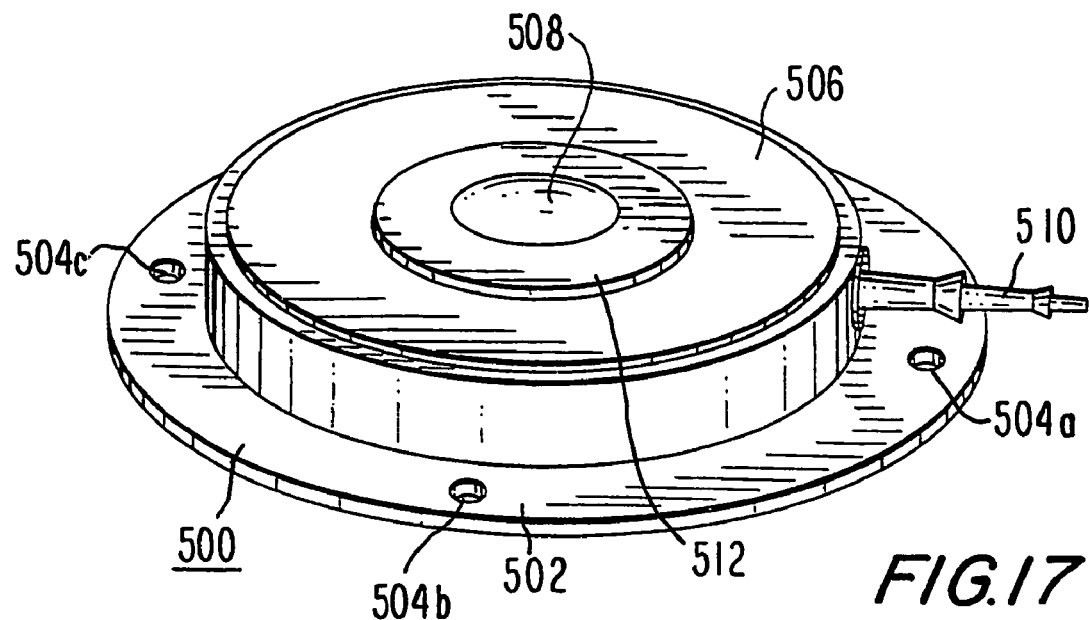
FIG. 17 is a schematic perspective representation of a VAP incorporating a magnetic alignment device in accordance with a seventh embodiment of the invention.

To that end, this embodiment of the invention comprises a novel implantable device with a lower profile that uses magnetic alignment to ensure accurate alignment and transdermal coupling between the septum and the administration apparatus. This aspect of the invention is illustrated in FIG. 17, which is a perspective schematic representation of a VAP 500 incorporating a magnetic alignment device. As in prior art devices, an attachment flange 502 includes suture holes 540a, 504b, and 504c spaced equally around the flange periphery (the fourth hole cannot be seen in this depiction). A septum 508 of a suitable material provides access to a plenum 506, from which leads a tubing connector 510, essentially as in a conventional VAP as seen in FIG. 16. However, unlike the prior art, the VAP of the present invention includes a ring-shaped aligning magnet 512 surrounding the septum 508. Because the magnet 512 permits accurate alignment and coupling of an administration apparatus with a hypodermic needle in a manner to be described, the plenum 506 can have a lower profile than in prior art VAPs.

Figure 18:
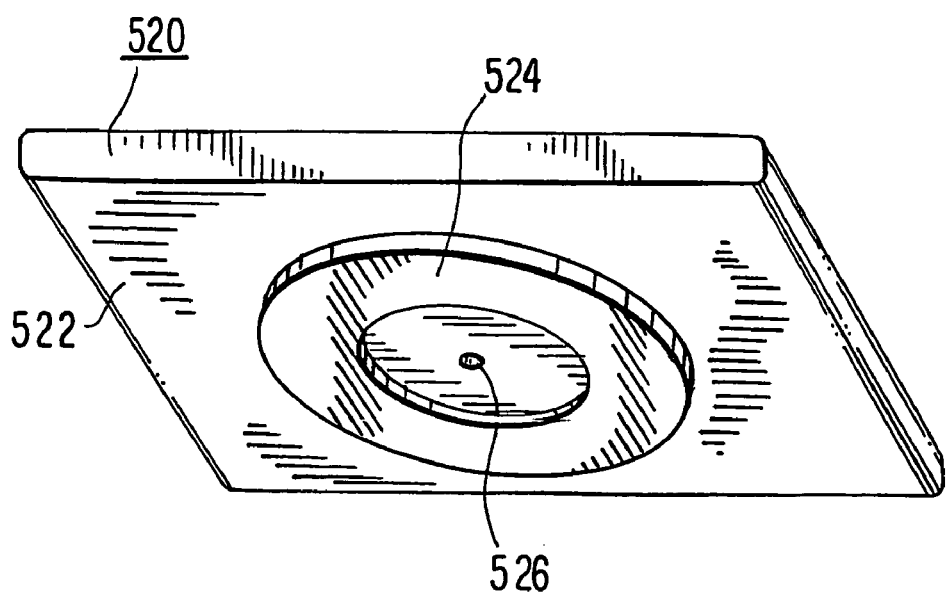
FIG. 18 is a schematic perspective representation of a syringe locating tool used in conjunction with the VAP shown in FIG. 17.

The VAP 500 will typically be used with a coupling device such as the coupling tool 520 depicted schematically in FIG. 18. This tool comprises a compliant base plate 522 that will conform somewhat to the contour of the patient's body at the site of the implanted VAP. Mounted on the base plate is a ring-shaped magnetic member 524, which preferably is a permanent magnet. It is generally of the same dimensions as the aligning magnet 512 on the VAP 500. A hole 526 for a hypodermic needle is disposed in the center of the ring-shaped magnetic member 524. The magnetic member 524 can be a non-magnetized magnetically permeable material, but for maximum coupling strength to the magnet 512, the member 524 is preferably also a permanent magnet. In addition, the magnetic member 512 on the VAP could be a non-magnetized magnetically permeable material, with the magnetic member 524 being a magnet, but again, two magnets are preferred.

In use, with the VAP 500 already implanted in the patient and the tubing connector in communication with a vein, or other vascular or anatomical structure, internally of the patient, the coupling tool 520 is placed on the patient with the magnet side in contact with the patient's skin, in the known vicinity of the implanted VAP. The coupling tool is moved slowly across the patient's skin, and when the two magnets 512 and 524 are magnetically coupled, the tool is held in place magnetically with the needle hole 526 in alignment with the septum 508. (FIG. 18 shows the magnetic member 524 slightly raised from the surface of the base 522, but it can be made flush with the base to facilitate movement of the device over the patient's skin.) The medication can then be introduced through the hole 526. The coupling tool can be made cheaply enough to be disposable, thus avoiding the necessity of repeatedly sterilization. In another variation, the coupling tool can include an adapter into which the administration apparatus be secured with the needle thereof in precise alignment with the hole 526. For example, the adapter can include a snap detent arrangement that cooperates with structure on the administration apparatus to snap the apparatus in place on the tool before it is used to locate the implanted VAP.

It will be appreciated that this is an improvement over prior art VAP locating arrangements, such as that described in U.S. Pat. No. 5,758,667, discussed above. In that patent, a locating device placed on the patient's skin indicates the general direction of the septum in the implanted dispensing device. However, simply indicating on the skin a point that overlies the septum does not ensure that the septum will be punctured by the needle, one reason being that the skin can move relative to deeper anatomical structures where the VAP is secured. On the other hand, the device according to this embodiment of the present invention is directly coupled to the VAP, and "locks" the injection site into place relative to the septum.

Those skilled in the art will immediately recognize that this aspect of the invention can be used with other types of implanted devices without departing from the spirit of the invention. For example, the principles underlying this aspect of the invention are applicable to dialysis patients, and the administration of analgesics, chemotherapeutic, antibiotics, etc. They can be incorporated into devices for the intravascular introduction of nutritional support or other substances to specific anatomical regions, such as the gastrointestinal tract, urinary bladder, renal pelvis, uterus, cerebrospinal fluid-containing spaces, etc.

The transdermal magnetic coupling aspects of the invention has applications in other areas as well. Transdermally coupled components can be used with ostomies at the skin level that provide access to internal body cavities such as the bowel or stomach. Taking as an example a bowel ostomy, a ring-shaped magnetic member may be implanted subcutaneously to surround the ostomy site. An ostomy appliance and or lavage apparatus could then incorporate a cooperating magnetic member that magnetically couples to the implanted member. A cap with a cooperating magnetic member could be employed to close the ostomy.

Magnetic Implanting Device and Method

Figure 19:
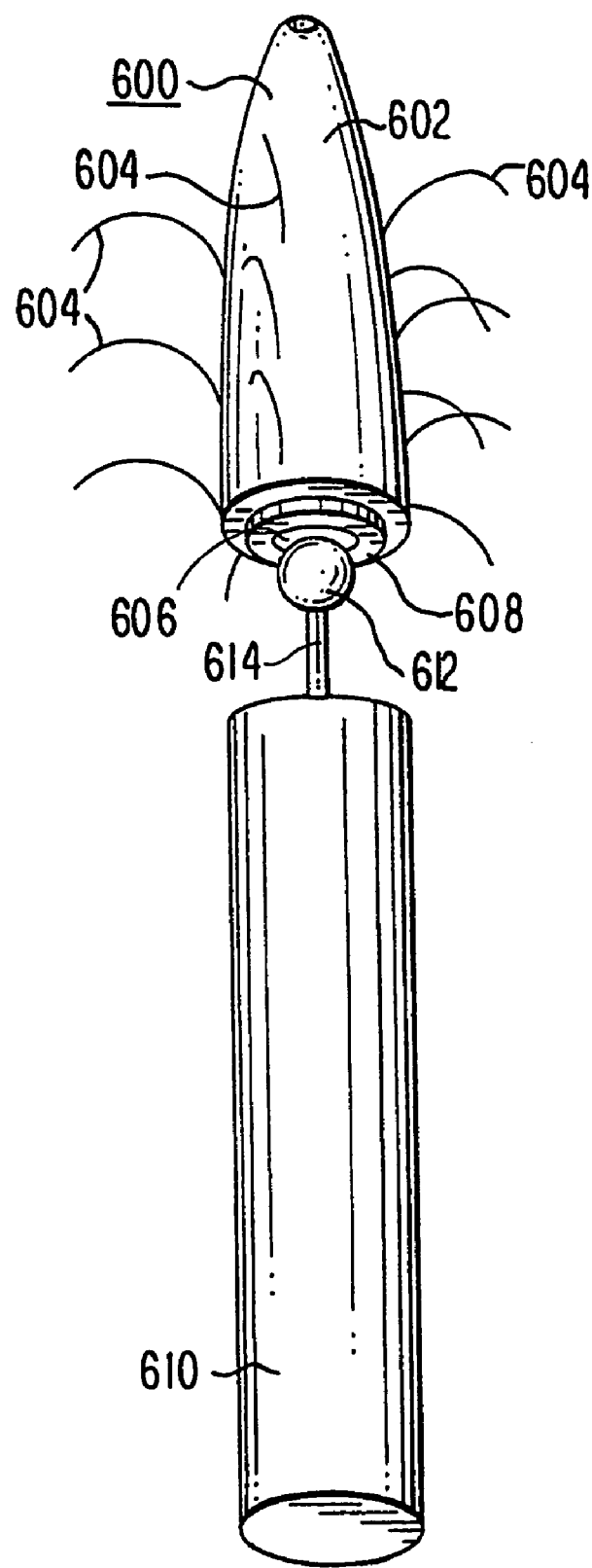
Figure 20:
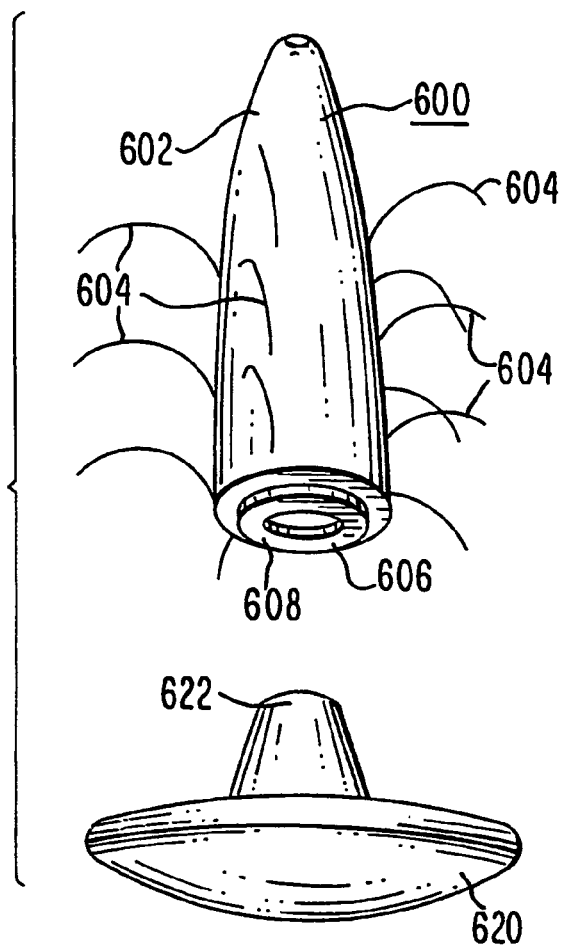
Figure 21:
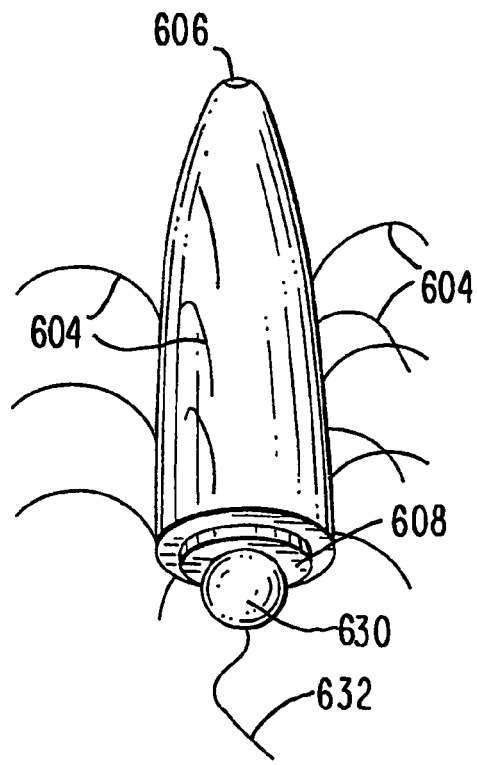

A final example of the versatility of the broad concept underlying the present invention is illustrated in FIGS. 19 to 21. This aspect of the invention is described as being applied to an ostium plug used to block the Fallopian tubes in a known sterilization procedure.

FIG. 19 is a perspective schematic representation of an ostium plug device 600 adapted from prior art ostium plugs. As in prior art plugs, the plug body 602 is has a gently narrowing profile for ease of insertion into the tubal ostia, with small barbs 604 that engage the tube walls upon insertion. These barbs, along with other biomaterials incorporated in the plug, induce the formation of fibrous connective tissue which secures the plug and completely occludes the tube. Unlike prior art plugs, the plug 600 has a lumen 606 extending axially of the plug, with a ring-shaped magnetic member 608 surrounding the lumen at the proximal end of the plug body 602. An insertion device 610 is introduced transcervically into the patient's uterus using hysteroscopic or fluoroscopic guidance techniques, with the plug 600 held at its proximal end by a ball-shaped member 612, which may be a magnet that couples weakly to the ring-shaped magnetic member 608 on the plug. As before, one or both of the magnetic members can be a permanent magnet made of the materials discussed above and coated with a biocompatible material. If only one of the members is a magnet, the other is a magnetically permeable material of the type also discussed previously. When the distal end of the plug body is in position, the surgeon extends an implanting push-rod 614 to manipulate the plug into the ostium. When the push rod is withdrawn, the magnetic members separate because of the engagement of the barbs with the tube walls. Alternatively, the magnetic member 612 can be an electromagnet that is de-energized when the plug is in place. (Those skilled in the art will recognize that any of the preceding embodiments could employ electromagnets instead of permanent magnets for applications when that would be advantageous to carrying out the objects of the invention.)

In the condition shown in FIG. 19, the patient can still conceive because of the lumen in the plug body 602. A transcervical coupler may be used to magnetically couple a flushing catheter to the plug for cleaning of the lumen of the plug when necessary. A cap 620 with a magnetic member 622 that fits within the proximal end of the lumen 606 can be introduced to effect sterilization. In accordance with principles discussed previously, more secure attachment of the cap to the plug will be effected if both the magnetic members 608 and 622 are permanent magnets. In addition, the use of magnetic members will assist in properly aligning the cap magnetic member 624 with the plug magnetic member 608, thus facilitating the sterilization procedure. Reversal thereof is effected simply by removing the cap 620, and performing the necessary procedure to ensure that the lumen is free from occlusion. In that regard, a flushing catheter as described above may be used for that purpose..

FIG. 21 shows an alternate blocking member 630 in the form of a ball-shaped magnetic member 632. The ball 630 can be used instead of the cap 620 to block the plug lumen 606. The ball can include a tether filament 632 that can be grasped by a surgical instrument (not shown) when the sterilization is to be reversed.

Those skilled in the art will readily appreciate that this aspect of the invention is not limited to implanting ostium plugs, but has wider uses in device implantation. In addition, although it is particularly adapted for reversal sterilizations, conventional ostium plugs without lumens can be implanted by the procedure described in connection with FIG. 19.

SUMMARY

Those skilled in the art will readily recognize that the principles underlying the present invention has application to a wide variety of apparatus.

In that connection, only selected preferred embodiments of the invention have been depicted and described, and it will be understood that various changes and modifications can be made other than those specifically mentioned above without departing from the spirit and scope of the invention, which is defined solely by the claims that follow.

What is claimed is:

1. A trocar assembly comprising:
a trocar including an elongated, generally annular cannula for extending through a tissue boundary, said cannula having a distal end for placement on one side of the tissue boundary and a proximal end for placement on another side of the tissue boundary, a trocar base disposed at said proximal end of said cannula, and a trocar lumen extending from a proximal end of said base axially through said cannula to said distal end thereof; and
a trocar cap for removable attachment to said proximal end of said trocar base, said cap having a cap lumen, wherein:
said trocar includes a magnet comprising an annular disc disposed at said proximal end of said base surrounding said trocar lumen;
said trocar cap includes a magnetic member comprising a second magnet or a non-magnetized magnetically permeable member, said magnet on said trocar and said magnetic member on said cap being positioned on said cap and said trocar for magnetically securing said cap to said proximal end of said trocar base with said cap lumen in alignment with said trocar lumen; and
said trocar cap and said trocar base include cooperating camming members for generating a force tending to separate said cap and said base upon movement of said cap transversely to said base.

2. A trocar assembly as in claim 1, wherein said magnet on said trocar comprises a permanent magnet and said magnetic member on said cap comprises a permanent magnet, the magnetic fields of said magnets being oriented to attract a predetermined side of said cap to said base.

3. A trocar assembly as in claim 1, wherein said trocar cap magnetic member is a magnet.

4. A trocar assembly as in claim 3, wherein said trocar cap magnet is funnel-shaped and surrounds said cap lumen.

5. A trocar assembly as in claim 3, wherein said trocar cap magnet creates a magnetic field generally axially aligned with said cap lumen and having a predetermined strength for holding a distal end of an elongated surgical instrument in place in alignment with said cap lumen.

6. A trocar assembly as in claim 5, wherein said cap lumen forms a funnel-shaped opening at a proximal end of said cap.

7. A trocar assembly as in claim 3, wherein said trocar cap magnet comprises one of an annular disc surrounding said cap lumen and a plurality of individual elements secured to said cap and arranged circumferentially around said cap lumen.

8. A trocar assembly as in claim 7, wherein said cap lumen forms a funnel-shaped opening at a proximal end of said cap.

9. A trocar assembly as in claim 1, wherein:
said trocar cap magnetic member comprises an annular disc secured to said cap surrounding said cap lumen, and said trocar cap camming member further includes an annular cap camming ring surrounding said annular disc and having a first sloped face; and
said trocar base camming member includes an annular trocar camming ring surrounding said annular disc and having a second sloped face for cooperating with said first sloped face for generating a force tending to separate said cap and said base upon movement of said cap transversely to said base.

10. A trocar assembly as in claim 9, wherein said camming rings are compliant to form a circumferential seal between said contacting sloped faces when said cap is magnetically secured to said base.

11. A trocar assembly comprising:
a trocar including an elongated, generally annular cannula for extending through a tissue boundary, said cannula having a distal end for placement on one side of the tissue boundary and a proximal end for placement on another side of the tissue boundary, a trocar base disposed at said proximal end of said cannula, and a trocar lumen extending from a proximal end of said base axially through said cannula to said distal end thereof; and
a trocar cap for removable attachment to said proximal end of said trocar base, said cap having a cap lumen, wherein:
said trocar includes a magnet comprising an annular disc disposed at said proximal end of said base surrounding said trocar lumen;
said trocar cap includes a magnetic member comprising a second magnet or a non magnetized magnetically permeable member, said magnet on said trocar and said magnetic member on said cap being positioned on said cap and said trocar for magnetically securing said cap to said proximal end of said trocar base with said cap lumen in alignment with said trocar lumen; and
said trocar assembly further comprises at least one of a cap valve member including a compliant toroidal body disposed in said cap and a trocar valve member including a compliant toroidal body disposed in said trocar base, wherein said toroidal body has a central opening and is disposed for compression axially when said cap is magnetically secured to said base thereby closing said central opening when a surgical instrument is not present in said lumen.

12. A trocar assembly as in claim 11, further comprising said cap valve member and said trocar valve member, wherein said toroidal bodies are in contact to mutually compress each other axially when said cap is magnetically secured to said base.

13. A trocar as in claim 11, wherein at least one of said compliant toroidal body disposed in said cap and said compliant toroidal body disposed in said trocar base comprises at least one of an elastomeric material, silicone rubber, and a hollow compliant material filled with at least one of a sterile saline solution and a hydrogel.

14. A trocar comprising;
an elongated cannula for extending through a tissue boundary, said cannula having a distal end for placement on one side of the tissue boundary and a proximal end for placement on another side of the tissue boundary, and a trocar base disposed at said proximal end of said cannula, with a trocar lumen extending axially of said base from a proximal end thereof to said distal end of said cannula; and
a magnet in said base comprising an annular disc disposed at said proximal end of said base surrounding said lumen creating a magnetic field generally axially aligned with said lumen and having a predetermined strength for holding a distal end of an elongated surgical instrument in place in alignment with said lumen, wherein said lumen forms a funnel-shaped opening at said base that narrows along said lumen in a direction away from said proximal end of said base.

15. A trocar comprising;
an elongated cannula for extending through a tissue boundary, said cannula having a distal end for placement on one side of the tissue boundary and a proximal end for placement on another side of the tissue boundary, and a trocar base disposed at said proximal end of said cannula, with a trocar lumen extending axially of said base from a proximal end thereof to said distal end of said cannula; and
a magnet in said base including an annular member surrounding said lumen creating a magnetic field generally axially aligned with said lumen and having a predetermined strength for holding a distal end of an elongated surgical instrument in place in alignment with said lumen,
wherein said lumen forms a funnel-shaped opening at said base that narrows along said lumen in a direction away from said proximal end of said base.

16. A trocar as in claim 15, wherein said magnet is funnel-shaped to form said opening.

17. A trocar as in claim 16, wherein said magnet completely surrounds said funnel-shaped opening.

18. A trocar as in claim 15, wherein said magnet completely surrounds said lumen.

19. A trocar as in claim 15, wherein said magnet is circular.

20. A trocar as in claim 15, wherein said magnet comprises an annular disc.

21. A trocar as in claim 20, wherein said annular disc completely surrounds said lumen.

22. A trocar as in claim 21, wherein said annular disc is circular.

* * * * *